(12) United States Patent
Mitra et al.

(10) Patent No.: US 9,611,353 B2
(45) Date of Patent: Apr. 4, 2017

(54) DRUG LOADING PENTABLOCK POLYMERS

(71) Applicant: THE CURATORS OF THE UNIVERSITY OF MISSOURI, COLUMBIA, MO (US)

(72) Inventors: Ashim K. Mitra, Overland Park, KS (US); Sulabh P. Patel, Kansas City, MO (US); Ravi D. Vaishya, Kansas City, MO (US); Vibhuti Agrahari, Kansas City, MO (US)

(73) Assignee: THE CURATORS OF THE UNIVERSITY OF MISSOURI, Columbia, MO (US)

(*) Notice: Subject to any disclaimer, the term of this patent is extended or adjusted under 35 U.S.C. 154(b) by 0 days.

(21) Appl. No.: 14/891,574

(22) PCT Filed: May 16, 2014

(86) PCT No.: PCT/US2014/038340
§ 371 (c)(1),
(2) Date: Nov. 16, 2015

(87) PCT Pub. No.: WO2014/186669
PCT Pub. Date: Nov. 20, 2014

(65) Prior Publication Data
US 2016/0090444 A1 Mar. 31, 2016

Related U.S. Application Data

(60) Provisional application No. 61/824,063, filed on May 16, 2013, provisional application No. 61/883,539, filed on Sep. 27, 2013.

(51) Int. Cl.
*C08G 63/91* (2006.01)
*A61K 9/06* (2006.01)
*A61K 9/51* (2006.01)
*C08G 63/664* (2006.01)

(52) U.S. Cl.
CPC .............. *C08G 63/912* (2013.01); *A61K 9/06* (2013.01); *A61K 9/5153* (2013.01); *A61K 9/5192* (2013.01); *C08G 63/664* (2013.01)

(58) Field of Classification Search
CPC ...... A61K 9/06; A61K 9/5153; A61K 9/5192; C08G 63/664; C08G 63/912
See application file for complete search history.

(56) References Cited

U.S. PATENT DOCUMENTS

| | | | |
|---|---|---|---|
| 5,442,016 A | 8/1995 | Jarrett et al. | |
| 5,702,717 A * | 12/1997 | Cha ................ | A61K 9/0024 424/424 |
| 6,056,970 A | 5/2000 | Greenawalt et al. | |
| 6,201,072 B1 | 3/2001 | Rathi et al. | |
| 6,410,645 B1 | 6/2002 | Pathak et al. | |
| 6,800,663 B2 | 10/2004 | Asgarzadeh et al. | |
| 7,879,270 B2 | 2/2011 | Varma et al. | |
| 2004/0185104 A1 | 9/2004 | Piao et al. | |
| 2005/0238722 A1 | 10/2005 | Pathak et al. | |
| 2006/0034889 A1 | 2/2006 | Jo et al. | |
| 2007/0244259 A1 | 10/2007 | Lee et al. | |
| 2008/0293827 A1 | 11/2008 | Lee et al. | |
| 2011/0034623 A1 | 2/2011 | Balk et al. | |
| 2011/0071216 A1 | 3/2011 | Fowers et al. | |
| 2011/0250283 A1 | 10/2011 | Mitra et al. | |

FOREIGN PATENT DOCUMENTS

| | | |
|---|---|---|
| EP | 0558965 | 9/1993 |
| WO | WO 2006/109945 | 10/2006 |
| WO | WO 2009/126442 | 10/2009 |
| WO | WO 2011/035264 | 3/2011 |
| WO | WO 2013/055331 | 4/2013 |

OTHER PUBLICATIONS

Deng et al. (Journal of Polymer Science: Part A: Polymer Chemistry, vol. 35, 703-708 (1997).*
Sawhney et al., "Rapidly degraded terpolymers of dl-lactide, glycolide, and ε-caprolactone with increased hydrophilicity by copolymerization with polyethers", Journal of Biomedical Materials Research, vol. 24, pp. 1397-1411 (1990), 15 pgs.
International Search Report and Written Opinion for related PCT/US11/55970 dated Mar. 2, 2012, 11 pgs.
Deng, et al., "Synthesis and Characterization of Biodegradable Block Copolymers of ε-Caprolactone and D, L-Lactide Initiated by Potassium Poly(ethylene glycol)ate", Journal of Polymer Science: Part a: Polymer Chemistry, vol. 35, pp. 703-708 (1997), 6 pgs.
Soo, et al., "The Synthesis and Biodegradation of PLA-PCL-PEG-PCL-PLA Multi Block Copolymer", Polymer Preprints, Japan 49, No. 2 (2000) [abstract only], 1 pg.
Huang, "Polymeres Bioresorbables Derives de Poly(ε-Caprolactone) en Ingenierie Tissulaire", Thesis, Dec. 2004, 177 pgs.
Huang, "Polymeres Bioresorbables Derives de Poly(ε-Caprolactone) en Ingenierie Tissulaire", PowerPoint, Dec. 2004, downloaded from web site www.huangminghsi.com/minghsi/these_orale.pdf on Apr. 21, 2008—no longer available, 5 pgs.
Hwang, "Caprolactonic Poloxamer Analog: PEG-PCL-PEG", Biomacromolecules, vol. 6, No. 2, 2005, 6 pgs.

(Continued)

*Primary Examiner* — Anna Falkowitz
(74) *Attorney, Agent, or Firm* — Stinson Leonard Street LLP

(57) ABSTRACT

Novel pentablock polymers having a PCL-PLA-PEG-PLA-PCL or PCL-PGA-PEG-PGA-PCL configuration, wherein PEG is polyethylene glycol, PCL is poly(δ-caprolactone), PGA is poly(glycolic acid), and PLA is poly(lactic acid), and methods of making nanoparticles from the pentablock polymers, are disclosed. The invention is also directed to a method for preparing nanoparticle compositions comprised of polymers with high levels of bioactive or diagnostic agents.

26 Claims, 8 Drawing Sheets

(56) References Cited

OTHER PUBLICATIONS

Huang, et al., "Degradation Characteristics of Poly(ε-caprolactone)-Based Copolymers and Blends", Journal of Applied Polymer Science, vol. 102, pp. 1681-1687 (2006), 7 pgs.

Liu, et al., "Thermoreversible Gel-Sol Behavior of Biodegradable PCL-:EG-PCL Triblock Copolymer in Aqueous Solutions", Journal of Biomedical Materials Research Part B: Applied Biomaterials, pp. 165-175 (2007), 11 pgs.

Gong, et al., "Thermosensitive PEG-PCL-PEG Hydrogel Controlled Drug Delivery System: Sol-Gel-Sol Transition and In Vitro Drug Release Study", Journal of Pharmaceutical Sciences, vol. 98, No. 10, pp. 3707-3717 (2009), 11 pgs.

Gong, et al., "Synthesis and Characterization of PEG-PCL-PEG Thermosensitive Hydrogel", International Journal of Pharmaceutics, vol. 365, pp. 98-99 (2009), 11 pgs.

International Search Report and Written Opinion for related PCT/US14/38340 dated Oct. 8, 2014, 14 pgs.

Huang, et al., Synthesis and Characterization of Block Copolymers of ε-Caprolactone and DL-Lactide Initiated by Ethylene Glycol or Poly(ethylene glycol), Macromolecular Chemistry and Physics, vol. 204, pp. 1994-2001 (2003), 8 pgs.

Bilati, et al., "Poly(D,L-lactide-co-glycolide) Protein-Loaded Nanoparticles Prepared by the Double Emulsion Method—Processing and Formulation Issues for Enhanced Entrapment Efficiency", Journal of Microencapsulation, vol. 22(2), (Mar. 2005) pp. 205-214, 11 pgs.

Spada, et al., "Protein Delivery from Polymeric Nanoparticles", World Academy of Science, Engineering and Technology, vol. 76 (2011) pp. 245-249, 5 pgs.

Santander-Ortega, et al., "Protein-Loaded PLGA-PEO Blend Nanoparticles: Encapsulation, Release and Degradation Characteristics", Colloid Polym Sci, vol. 288 (2010) pp. 141-150, 10 pgs.

Tamboli, V., et al., "Novel Pentablock Copolymer (PLA-PCL-PEG-PCL-PLA)-based Nanoparticles for Controlled Drug Delivery: Effect of Copolymer Compositions on the Crystallinity of Copolymers and in Vitro Drug release Profile from Nanoparticles", Colloid Polym Sci (2013) 291:1235-1245 (12 pgs).

* cited by examiner

DRUG LOADING PENTABLOCK POLYMERS

CROSS-REFERENCE TO RELATED APPLICATIONS

This application is based on and claims priority to U.S. Provisional Application Ser. No. 61/824,063, filed on May 16, 2013, and U.S. Provisional Application Ser. No. 61/883,539, filed on Sep. 27, 2013, which are incorporated herein by reference in their entireties.

BACKGROUND OF THE INVENTION

1. Field of the Invention

The present invention relates to novel pentablock polymers useful for the administration of biologically active agents or diagnostic agents, especially hydrophilic compounds such as peptides and proteins, and nanoparticles comprising the polymers. The present invention is also directed to controlled release formulations comprising the nanoparticles dispersed in thermosensitive gels. Methods of making the nanoparticles are also described. The present invention is further directed to a method for preparing nanoparticulate compositions comprised of polymers with high levels of bioactive or diagnostic agents and the compositions obtained by such methods.

2. Description of Related Art

Various block polymers are known in the art. For example, Cha et al., U.S. Pat. No. 5,702,717 discloses several triblock polymers, such as the PCL-PEG-PCL and PLA-PEG-PLA triblock polymer comprised of polyethylene glycol ("PEG") and poly(ε-caprolactone) ("PCL"), and polylactide ("PLA"). See also Lui et al., *Thermoreversible gel-sol behavior of biodegradable PCL-PEG-PCL triblock copolymer in aqueous solutions*, J. Biomed. Mater. Res. B. Appl. Biomater. January 84 (1) 165-75 (2008). These polymers forming the block polymer are all well-known FDA-approved biodegradable and biocompatible materials. Recently, pentablock polymers having a PGA-PCL-PEG-PCL-PGA or PEG-PCL-PLA-PCL-PEG configuration have been investigated by certain of the present inventors as set forth in Mitra et al., U.S. Pat. No. 8,851,531.

BRIEF SUMMARY OF THE INVENTION

One aspect of the present invention is directed to novel pentablock polymers useful for the delivery of bioactive agents and/or diagnostic agents (especially proteins and peptides) useful in the treatment or diagnosis of a wide number of disorders or diseases.

In one aspect, the present invention is directed to novel pentablock polymers which are useful for forming nanoparticles with the bioactive agent and/or diagnostic agent encapsulated therein. The nanoparticles are ideal for drug delivery in which the drug release is expected to exhibit first order kinetics.

In one aspect, the pentablock polymers are defined according to the formula:

$$PCL_C\text{-}PLA_B\text{-}PEG_A\text{-}PLA_B\text{-}PCL_C,$$

wherein PEG is polyethylene glycol;
wherein PLA is polylactic acid;
wherein PCL is poly(ε-caprolactone);
wherein A defines an average molecular weight of 200 to 20,000 Da;
wherein B defines an average molecular weight of 100 to 10,000 Da; and
wherein C defines an average molecular weight of 500 to 25,000 Da.

In another aspect, the pentablock polymers are defined according to the formula:

$$PCL_F\text{-}PGA_E\text{-}PEG_D\text{-}PGA_E\text{-}PCL_F,$$

wherein PEG is polyethylene glycol;
wherein PGA is polyglycolic acid;
wherein PCL is poly(ε-caprolactone);
wherein D defines an average molecular weight of 200 to 20,000 Da;
wherein E defines an average molecular weight of 100 to 15,000 Da; and
wherein F defines an average molecular weight of 500 to 25,000 Da.

The nanoparticles may be combined with a thermosensitive gel, such as those described in Mitra et al., U.S. Pat. No. 8,851,531, which is incorporated by reference with respect to such disclosure. The thermosensitive gel preferably has a lower crucial solution temperature below body temperature, and most preferably below about 35° C. The thermosensitive gel is preferably an injectable drug delivery liquid composition having reverse thermal gelation properties comprising the thermosensitive pentablock polymers having a PEG-PCL-PLA-PCL-PEG configuration, a pharmaceutically acceptable liquid carrier, and an effective amount of a bioactive agent or diagnostic agent. In one aspect, the pentablock polymer comprising the thermosensitive gel comprises about 1 to 50 wt % of the composition. In still another aspect, the pharmaceutically acceptable liquids carrier is selected from the group consisting of PBS, saline, and dextrose solutions.

In still another aspect, the nanoparticles of the present invention and thermosensitive gel may be combined to form a controlled release formulation. In one aspect, the drug or diagnostic agent is encapsulated in the nanoparticles. In turn, these nanoparticles are dispersed in the thermosensitive gel. Thus, in one aspect, the present invention is directed to a controlled release formulation comprising a plurality of nanoparticles. The nanoparticles comprise a drug or diagnostic agent encapsulated in a pentablock polymer according to $PCL_{500\text{-}25,000}\text{-}PLA_{100\text{-}10,000}\text{-}PEG_{200\text{-}20,000}\text{-}PLA_{100\text{-}10,000}\text{-}PCL_{500\text{-}25,000}$ or $PCL_{500\text{-}25,000}\text{-}PGA_{100\text{-}15,000}\text{-}PEG_{200\text{-}20,000}\text{-}PGA_{100\text{-}15,000}\text{-}PCL_{500\text{-}25,000}$ or combinations thereof. These nanoparticles are then dispersed in a thermosensitive gel comprising second pentablock polymer.

In still a further aspect, the present invention is directed to various methods of delivering bioactive agents or diagnostic agents using the pentablock polymers of the present invention. Thus, in one aspect, the present invention is directed to a method for the parenteral delivery of a bioactive agent or diagnostic agent to a subject comprising: (a) providing a pharmaceutical composition comprising (1) nanoparticles having an effective amount of the bioactive agent or diagnostic agent encapsulated in a pentablock polymer according to $PCL_{500\text{-}25,000}\text{-}PLA_{100\text{-}10,000}\text{-}PEG_{200\text{-}20,000}\text{-}PLA_{100\text{-}10,000}\text{-}PCL_{500\text{-}25,000}$ or $PCL_{500\text{-}25,000}\text{-}PGA_{100\text{-}15,000}\text{-}PEG_{200\text{-}20,000}\text{-}PGA_{100\text{-}15,000}\text{-}PCL_{500\text{-}25,000}$ or combinations thereof, in which the nanoparticles are dispersed in (2) a thermosensitive gel, such as the pentablock polymer having the PEG-PCL-PLA-PCL-PEG configuration as set forth in Mitra et al., U.S. Pat. No. 8,851,531 and (b) administering the pharmaceutical composition to the patient. The composition is preferably administered to the subject intramuscularly or subcutaneously. In a preferred aspect, the method includes the steps of providing an injectable drug delivery liquid having reverse thermal gelation properties, wherein the thermosensitive gel pentablock polymer has a LCST below the body temperature of the subject. The method also includes the step of maintaining the drug delivery liquid at a temperature below the LCST of the pentablock polymer. Next, the method includes the step of injecting said drug delivery liquid parenterally into the subject to form a gel depot of said drug and pentablock polymer as the temperature of the liquid is raised by the body temperature of said subject to be above the LCST of said polymer.

Yet another aspect of the invention is directed to a method for preparing bioactive or diagnostic agent loaded polymer nanoparticles to obtain a high loading of bioactive or diagnostic agent, typically around 10 to 25%. The present invention is also directed to a bioactive or diagnostic agent loaded nanoparticulate composition comprising the polymer and the bioactive agent or diagnostic agent prepared by the methods in accordance with the present invention. The polymer may be a novel pentablock polymer of the present invention or another polymer as described herein.

In one aspect of the invention, the drug loading method includes the steps of providing a $W_1$ solution comprising a bioactive agent or diagnostic agent in an aqueous solution; providing an organic solution O comprising an organic solvent and a polymer; emulsifying the $W_1$ solution in the organic solution O to form a $W_1/O$ primary emulsion; emulsifying the primary emulsion in an external water phase solution $W_2$ to obtain a $W_1/O/W_2$ double emulsion; optionally diluting the $W_1/O/W_2$ double emulsion with an aqueous solution $W_3$ to form a diluted $W_1/O/W_2$ double emulsion; and isolating the bioactive or diagnostic agent loaded nanoparticles from the optionally diluted $W_1/O/W_2$ double emulsion. In an exemplary aspect, the polymer is defined according to $PLA_{100-20,000}$-$PCL_{500-20,000}$-$PEG_{100-10,000}$-$PCL_{500-20,000}$-$PLA_{100-20,000}$. The volume ratios of the emulsion process are such that loading of the bioactive or diagnostic agent is improved. For example, in a preferred aspect, the ratio of $W_1/O$ is about 1:2 to 1:6 and the $O/W_2$ ratio is about 1:1 to 1:9.

In another aspect, the present invention is directed to a method for improving or optimizing a loading of a bioactive agent or diagnostic agent in a polymer nanoparticulate formulation. The method includes the steps of (a) providing $W_1$ solution or suspension comprising a bioactive agent or diagnostic agent in an aqueous solution; (b) providing an organic solution O comprising an organic solvent and a polymer; (c) emulsifying said $W_1$ solution in said organic solution O to form a $W_1/O$ primary emulsion; (d) emulsifying said primary emulsion in an external water phase solution $W_2$ to obtain a $W_1/O/W_2$ double emulsion; (e) optionally diluting said $W_1/O/W_2$ double emulsion with an aqueous solution $W_3$ to form a diluted $W_1/O/W_2$ double emulsion; (f) evaporating organic solvent from said $W_1/O/W_2$ double emulsion to form an aqueous nanoparticle suspension (g) isolating said drug polymer nanoparticulate formulation from said aqueous nanoparticle suspension; and (h) measuring the loading of the bioactive agent or diagnostic agent in the nanoparticulate formulation. The method also includes repeating steps (a) to (h) while varying one or more parameters selected from the group consisting of: the molecular weight of the polymer, $W_1/O$ ratio (v/v), $O/W_2$ (v/v), $W_1/O/W_2$ (v/v/v), $W_1/W_2$ ratio (v/v), $W_1/W_3$ ratio (v/v), $W_2/W_3$ ratio (v/v), $W_1/(W_2+W_3)$, and the initial or nominal ratio of polymer to bioactive agent or diagnostic agent (w/w), and combinations thereof.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 5A is for $PLA_{3000}$-$PCL_{7000}$-$PEG_{2000}$-$PCL_{7000}$-$PLA_{3000}$ (Pentablock Polymer A), and FIG. 5B is for $PLA_{3000}$-$PCL_{7000}$-$PEG_{4000}$-$PCL_{7000}$-$PLA_{3000}$ (Pentablock Polymer B).

DETAILED DESCRIPTION OF PREFERRED EMBODIMENT

Figure 1:
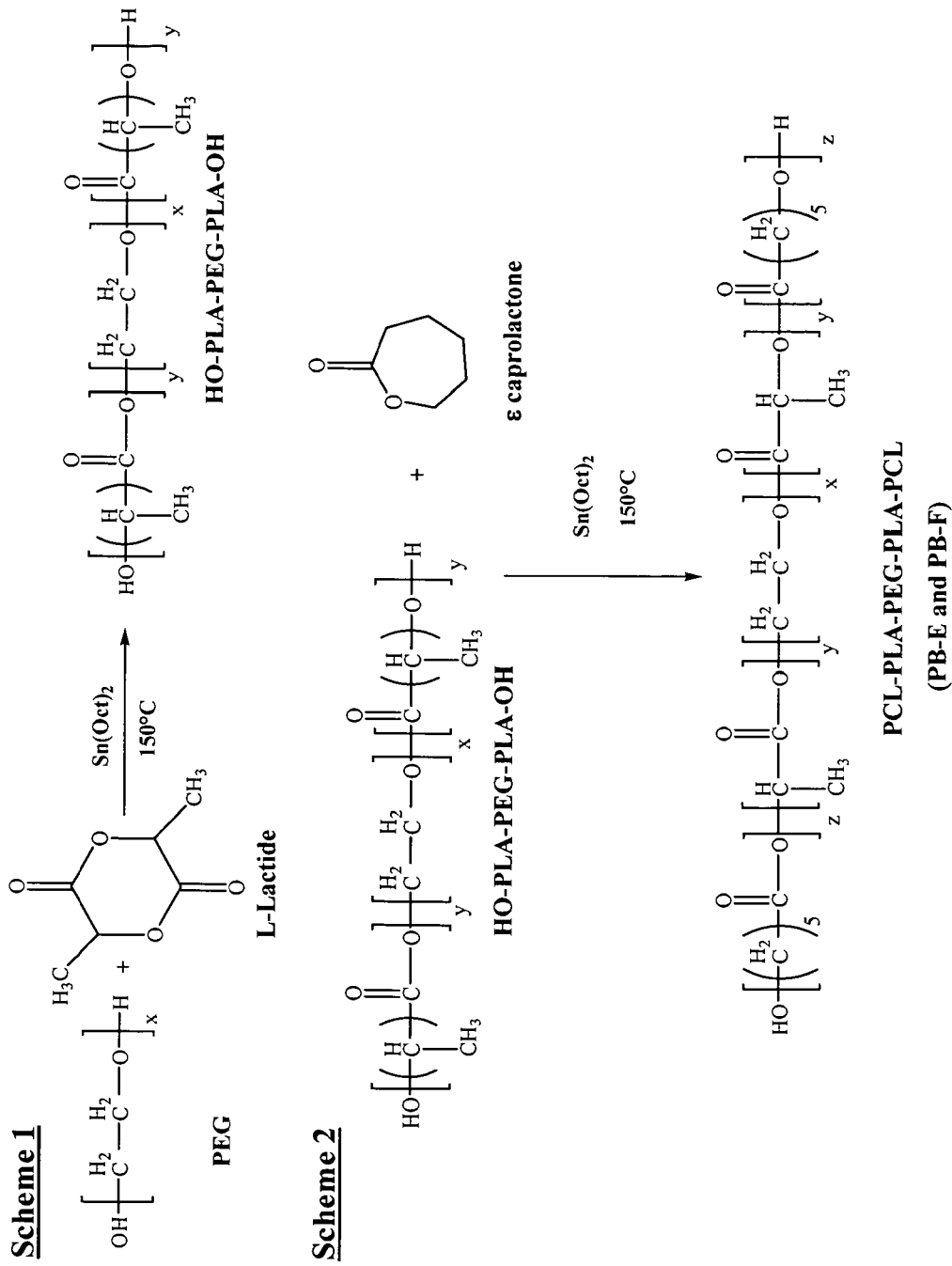
FIG. 1 shows the reaction scheme for the synthesis of polymers having a PCL-PLA-PEG-PLA-PCL configuration. Two pentablock polymers were prepared: $PCL_{7000}$-$PLA_{3000}$-$PEG_{4000}$-$PLA_{3000}$-$PCL_{7000}$ (Pentablock Polymer-E) and $PCL_{10,000}$-$PLA_{6000}$-$PEG_{4000}$-$PLA_{6000}$-$PCL_{10,000}$ (Pentablock Polymer F)

The present invention is directed to novel pentablock polymers useful for drug delivery systems. The polymers are biodegradable and biocompatible. Many of the pentablock polymers may be used to form nanoparticles with a bioactive agent or diagnostic agent contained therein. These nanoparticles may be incorporated into polymer solutions, especially pentablock polymer solutions, which exhibit reversible thermal sol-to-gel behavior, and possess good drug release characteristics.

The present invention is also directed to methods for fabricating the pentablock polymers of the present invention, as well as compositions comprising the biodegradable and biocompatible pentablock polymers with a hydrophilic drug, such as peptides and proteins. The present invention is well adapted for the administration of the hydrophilic drugs and particularly highly water-soluble peptide and protein drugs. However, the present invention may also be used to administer hydrophobic molecules. The drugs are released at a controlled rate with the corresponding biodegradation of the polymeric matrix.

The present invention is directed to a double emulsion solvent evaporation method for preparing nanoparticulate compositions comprised of biocompatible and biodegradable polymers with high loadings of bioactive or diagnostic agents and the compositions obtained by such methods.

As used herein, "administering" and similar terms mean delivering the composition to an individual being treated. Preferably, the compositions comprising the pentablock polymers of the present invention and any bioactive or diagnostic agents are administered by the subconjunctival, intravitreal, subcutaneous, intramuscular, transdermal, oral, transmucosal, or intraperitoneal routes. The administration may include delivery into the synovial space (e.g., for the treatment of arthritis), intrathecal injection (e.g., for the treatment of brain diseases), topical delivery (e.g., for the treatment of infectious skin diseases), topical nasal delivery, topical ocular delivery, subcutaneous injection for systemic delivery, and the like.

"Biocompatible" means materials or the intermediates or end products of materials formed by solubilization hydrolysis, or by the action of biologically formed entities which can be enzymes or other products of the organism and which cause no adverse effect on the body.

"Biodegradable" means that the polymer can break down or degrade within the body to non-toxic components after all bioactive agent or diagnostic agent has been released.

"Depot" means a drug delivery liquid following injection into a warm-blooded animal which has formed a gel upon the temperature being raised to or above the LCST.

"Drug" or "bioactive agent" or "diagnostic agent" shall mean any inorganic or organic compound or substance having bioactivity and adapted or used for a therapeutic or diagnostic purpose.

"Drug delivery liquid" or "drug delivery liquid having reverse thermal gelation properties" shall mean a "solution" suitable for injection into a warm-blooded animal which forms a depot upon having the temperature raised above the LCST of the polymer.

An "effective amount" means the amount of bioactive agent or diagnostic agent that is sufficient to provide the desired local or systemic effect at a reasonable risk/benefit ratio as would attend any medical treatment or diagnostic test. This will vary depending on the patient, the disease, the treatment being effected, and the nature of the agent.

"Gel," when used in reference to the pentablock polymers and/or drug combination at a temperature at or above the LCST, shall be inclusive of such combinations which are generally semi-solid in nature.

"Hydrophilic" means the ability to dissolve in water. When used in the context of the hydrophilic drugs or diagnostic agents in the present invention, the term embraces an agent that is preferably sparingly soluble, more preferably soluble, still more preferably freely soluble, and still most preferably very soluble, according to USP-NF definitions.

"LCST" or "lower critical solution temperature," means the temperature at which the pentablock polymer undergoes reverse thermal gelation, i.e., the temperature below which the polymer is soluble in water and above which the pentablock polymer undergoes phase separation to form a semi-solid containing the drug and the pentablock polymer. The terms "LCST," "gelation temperature," and "reverse thermal gelation temperature," or the like shall be used interchangeably in referring to the LCST.

The term "nanoparticle" or variations thereof (such as "nanoparticulate") generally refers to a particle, the largest dimension of which is less than one micron, e.g., less than about 1,000 nm, 900 nm, 800 nm, 700 nm, 600 nm, 500 nm, 400 nm, 300 nm, 200 nm, 100 nm, 50 nm, etc. Thus, for example, the nanoparticles of the present invention may range between about 100 to 1,000 nm, 200 to 900 nm, 300 to 700 nm, 400 to 600 nm, 400 to 900 nm or 450 to 850 nm.

"Parenteral" shall mean any route of administration other than the alimentary canal and shall specifically include intramuscular, intraperitoneal, intra-abdominal, subcutaneous, and, to the extent feasible, intravenous.

"Pharmaceutically acceptable" means that which is useful in preparing a pharmaceutical composition that is generally safe, non-toxic, and neither biologically nor otherwise undesirable and includes that which is acceptable for veterinary use as well as human pharmaceutical use. Examples of "pharmaceutically acceptable liquid carriers" include water, organic solvents, gels, creams and the like. Preferred pharmaceutically acceptable aqueous liquids include PBS, saline, and dextrose solutions.

"Peptide", "polypeptide", "oligopeptide," and "protein" shall be used interchangeably when referring to peptide or protein agents and shall not be limited as to any particular molecular weight, peptide sequence or length, field of bioactivity, diagnostic use, or therapeutic use unless specifically stated.

However, preferred proteins and peptides have molecular weights ranging from about 1 kDa to 500 kDa (e.g., about 1, 10, 50, 100, 150, 200, 250, 300, 350, 400, 450, or 500 kDa or some range therebetween).

"Solution," "aqueous solution," and the like, when used in reference to a combination of drug and pentablock polymer contained in such solution, shall mean a water-based solution having such drug/polymer combination dissolved or uniformly suspended therein at a functional concentration and maintained at a temperature below the LCST of the block polymer.

The term "thermosensitive" refers to a polymer which exists as a generally clear solution near ambient temperature in water but when the temperature is raised to the LCST (which is preferably about body temperature), interact to form a gel, emulsion, or suspension.

The term "treatment" or "treating" means administration of a drug for purposes including: (i) preventing the disease or condition, that is, causing the clinical symptoms of the disease or condition not to develop; (ii) inhibiting the disease or condition, that is, arresting the development of clinical symptoms; and/or (iii) relieving the disease or condition, that is, causing the regression of clinical symptoms.

Below, the exemplary embodiments are shown and specific language will be used herein to describe the same. It should nevertheless be understood that no limitation of the scope of the invention is thereby intended. Alterations and further modifications of the inventive features illustrated herein, and additional applications of the principles of the present invention as illustrated herein, for one skilled in the relevant art, in connection with this disclosure, should be considered within the scope of the present invention.

The present invention is directed to a novel pentablock polymer comprised of (1) PEG, (2) PCL, and (3) PGA or PLA. Generally, the block polymer will be a pentablock polymer, i.e., a CBABC type block polymer.

Polymers and Nanoparticles

For preparation of the pentablock polymer used for nanoparticles of the present invention, the pentablock polymer preferably has a PCL-PLA-PEG-PLA-PCL or PCL-PGA-PEG-PGA-PCL configuration.

The hydrophilic A block segment is preferably PEG having an average molecular weight of between about 200 to 20,000 Da (e.g., about 200, 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000 Da or some range therebetween) and more preferably has an average molecular weight between about 1,000 and 10,000 Da, and still more preferably has an average molecular weight between about 2,000 to 6,000 Da, and most preferably has an average molecular weight of about 4,000 Da.

The hydrophobic B block segment is preferably derived from a lactide or glycolide. In one aspect, the B block segment preferably comprises PLA having an average molecular weight of between about 100 to 10,000 Da (e.g., about 100, 500, 1,000, 2,000, 3,000, 4,000, 5,000, 6,000, 7,000, 8,000, 9,000, 10,000 Da or some range therebetween) and more preferably between about 1,000 and 8,000 Da, and still more preferably between about 3,000 and 6,000 Da. In another aspect, the hydrophobic B block segment comprises PGA having an average molecular weight of between about 100 to 15,000 Da (e.g., about 100, 500, 1,000, 2,000, 3,000, 4,000, 5,000, 6,000, 7,000, 8,000, 9,000, 10,000, 11,000, 12,000, 13,000, 14,000, 15,000 Da or some range therebetween) and more preferably between about 2,000 and 10,000 Da, and still more preferably between about 3,000 and 6,000 Da.

The hydrophobic C block segment is preferably derived from a cyclic lactone, and is most preferably derived from ε-caprolactone. Thus, the C block segment comprises PCL having an average molecular weight of between about 500 Da to 25,000 Da (e.g., about 500, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000 Da or some range therebetween), more preferably between about 3,000 to 15,000 Da, still more preferably about 6,000 to 12,000 Da, and most preferably about 7,000 to 10,000 Da.

Thus, in one aspect, a pentablock polymers used to make nanoparticles in accordance with the present invention may be defined according to the following formula:

H—[—O—(CH$_2$)$_5$—CO—]$_C$—[—O—CH(CH$_3$)—CO—]$_B$—[—O—CH$_2$—CH$_2$—]$_A$—[—O—CO—CH(CH$_3$)—]$_B$—[—O—CO—(CH$_2$)$_5$—]$_C$—OH wherein A, B, and C are integers such that the polymer can be defined according to:

PCL$_C$-PLA$_B$-PEG$_A$-PLA$_B$-PCL$_C$, wherein A defines an average molecular weight of 200 to 20,000 Da, preferably 1,000 to 10,000 Da, still more preferably 2,000 to 6,000 Da, and most preferably 4,000 Da;

wherein B defines an average molecular weight of 100 Da to 10,000 Da, preferably 1,000 to 8,000 Da, and still more preferably 3,000 to 6,000 Da; and wherein C defines an average molecular weight of 500 to 25,000 Da, preferably 3,000 to 15,000 Da, still more preferably 6,000 to 12,000 Da, and most preferably 7,000 to 10,000 Da.

In another aspect, a pentablock polymers used to make nanoparticles in accordance with the present invention may be defined according to the following formula:

H—[—O—(CH$_2$)$_5$—CO—]$_F$—[—O—CH$_2$—CO—]$_E$—[—O—CH$_2$—CH$_2$—]$_D$—[—O—CO—CH$_2$—]$_E$—[—O—CO—(CH$_2$)$_5$—]$_F$—OH wherein D, E, and F are integers such that the polymer can be defined according to:

PCL$_F$-PGA$_E$-PEG$_D$-PGA$_E$-PCL$_F$, wherein D defines an average molecular weight of 200 to 20,000 Da, preferably 1,000 to 10,000 Da, still more preferably 2,000 to 6,000 Da, and most preferably 4,000 Da;

wherein E defines an average molecular weight of 100 Da to 15,000 Da, preferably 2,000 to 10,000 Da, and still more preferably 3,000 to 6,000 Da; and wherein F defines an average molecular weight of 500 to 25,000 Da, preferably 3,000 to 15,000 Da, still more preferably 6,000 to 12,000 Da, and most preferably 7,000 to 10,000 Da.

By varying the molecular weights of the various A, B, and C blocks, the pentablock polymers synthesized as disclosed herein have various hydrophobic and hydrophilic blocks, which may alter how the nanoparticles degrade in vitro and in vivo. Nanoparticles generally will be formed if the ratio of the molecular weight of the hydrophobic blocks to the molecular weight of the hydrophilic blocks is greater than 3.

The hydrophilic A block and the hydrophobic B and C blocks are synthesized and utilized because of their biodegradable and biocompatible properties. The in vitro and in vivo degradation of these hydrophobic polymer blocks is well understood and the degradation products are natural metabolites that are readily eliminated by the body. Generally, for the preparation of nanoparticles, the hydrophilic A block (PEG block) should be less than about 30% by weight (e.g., less than about 30, 20, 15, or 10% by weight), the B block (PLA, PGA block) should be about 10 to 80% by weight (e.g., about 10, 20, 30, 40, 50, 60, 70 or 80% by weight), and the C block (PCL block) should about 10 to 80% by weight (e.g. about 10, 20, 30, 40, 50, 60, 70 or 80% by weight).

As shown in the examples, the pentablock polymer compounds of the present invention are ideally suited to form nanoparticles, which may encapsulate an effective amount bioactive agent or diagnostic agent. Examples of such agents are disclosed below. The nanoparticles comprising the pentablock polymers of the present invention provide for controlled or extended release of the bioactive agent or diagnostic agent. In general, the pentablock polymer can be designed to have a selected rate of drug release, and typically drug release from the nanoparticles exhibits first order drug release kinetics. The amount of drug or diagnostic agent loaded in the nanoparticles will depend upon the nature of the agent. However, the drug and/or diagnostic agent typically comprises about 0.01 to 50 wt % of the composition, more preferably about 0.1 to 10% wt of the composition, with about 1 to 5 wt % being most preferred.

Double Emulsion Solvent Evaporation on Method

The present invention is also directed to a double emulsion solvent evaporation method for preparing nanoparticulate compositions comprised of biocompatible and biodegradable polymers with high loadings of bioactive or diagnostic agents and the compositions obtained by such methods.

The nanoparticulate compositions preferably having a bioactive agent or diagnostic agent loading of about 10 to 25 wt % (e.g., about 10, 11, 12, 13, 14, 15, 16, 17, 18, 19, 20, 21, 22, 23, 24, 25 wt % or some range therebetween). In one aspect, bioactive agent or diagnostic agent loading is about 13 to 18 wt %.

The nanoparticulate compositions preferably having an entrapment efficiency of the bioactive agent or diagnostic agent which is greater than about 40% (e.g., greater than about 40, 45, 50, 55, 60, 65, 70, 75, 80, 85, 90% or some range therebetween). In one aspect, the entrapment efficiency of the bioactive agent or diagnostic agent is about 45% to 90%, and in another aspect, the entrapment efficiency is about 60% to 90%.

The nanoparticulate compositions are prepared by double emulsion solvent evaporation method. In general, the internal and external aqueous phases are separated by an oil layer. Surfactants and/or stabilizers may be utilized to assist with formation and stability. Surfactant(s) having a low HLB may be used to form the primary water in oil (w/o) emulsion and other surfactant(s) having a higher HLB to achieve secondary emulsification may be used to emulsify the water in oil emulsion into water. Exemplary surfactants and/or which may be used for emulsification in the preparation of the nanoparticles include dextran 70, Pluronic F68, polyvinyl alcohol (PVA), polyvinyl pyrrolidone (PVP), sorbitan esters (e.g., Span 20, Span 60, Span 65, Span 80), polysorbates (e.g., Tween 20, Tween 80), poloxamers (e.g., P188, P407), glyceryl monoesters, such as glyceryl monostearate, and nonyl phenol ethoxylates.

In the water/oil/water double emulsion solvent evaporation method, an aqueous solution or suspension of the drug (internal aqueous phase, $W_1$) is emulsified in a solution of polymer in organic solvent. The resulting primary emulsion ($W_1/O$) is then dispersed in a second aqueous phase (external aqueous phase, $W_2$) containing suitable emulsifier(s) to form double emulsion ($W_1/O/W_2$). The $W_1/O/W_2$ double emulsion is then optionally diluted with an aqueous phase $W_3$. Removal of the volatile organic solvent leads to the formation of solid nanoparticles. The solid nanoparticles are separated by filtration or centrifugation, and may be washed several times in order to eliminate the residual emulsifier and dried under vacuum or freeze-dried.

In one aspect, a method for preparing bioactive or diagnostic agent loaded nanoparticles is provided. The method comprises the steps of (a) emulsifying a $W_1$ solution in an organic solution O to form a $W_1/O$ primary emulsion, wherein the $W_1$ solution comprises a bioactive agent or diagnostic agent in an aqueous solution, and the organic solution O comprises an organic solvent and a polymer; (b) emulsifying the primary emulsion in an external water phase solution $W_2$ to obtain a $W_1/O/W_2$ double emulsion; (c) optionally diluting the $W_1/O/W_2$ double emulsion with an aqueous solution $W_3$ to form an optionally diluted $W_1/O/W_2$ double emulsion; and (d) removing the organic solvent from the optionally diluted $W_1/O/W_2$ double emulsion to form said bioactive or diagnostic agent loaded nanoparticles. The bioactive or diagnostic agent has a loading of about 10 to 25% in the polymer nanoparticles.

In another aspect, the method for preparing bioactive or diagnostic agent loaded nanoparticles may comprise the steps of (a) providing a $W_1$ solution comprising a bioactive agent or diagnostic agent in an aqueous solution; (b) providing an organic solution O comprising an organic solvent and a polymer; (c) emulsifying the $W_1$ solution in the organic solution O to form a $W_1/O$ primary emulsion; (d) emulsifying the primary emulsion in an external water phase solution $W_2$ to obtain a $W_1/O/W_2$ double emulsion; (e) optionally diluting the $W_1/O/W_2$ double emulsion with an aqueous solution $W_3$ to form an optionally diluted $W_1/O/W_2$ double emulsion; (f) evaporating organic solvent from said $W_1/O/W_2$ double emulsion to form an aqueous nanoparticle suspension; and (g) isolating the bioactive or diagnostic agent loaded nanoparticles from the aqueous nanoparticle suspension. The bioactive or diagnostic agent has a loading of about 10 to 25% in the polymer nanoparticles.

In a further aspect, a method for preparing a bioactive or diagnostic agent loaded nanoparticles is provided. The method comprises the steps of (a) emulsifying a $W_1$ solution in an organic solution O to form a $W_1/O$ primary emulsion, wherein the $W_1$ solution comprises a bioactive agent or diagnostic agent in an aqueous solution, and the organic solution O comprises dichloromethane as an organic solvent and a polymer according to $PLA_z\text{-}PCL_y\text{-}PEG_x\text{-}PCL_y\text{-}PLA_z$ or $PGA_z\text{-}PCL_y\text{-}PEG_x\text{-}PCL_y\text{-}PGA_z$ or combinations thereof, wherein X defines an average molecular weight of 100 to 10,000 Da, wherein Y defines an average molecular weight of 500 to 20,000 Da, and wherein Z defines an average molecular weight of 100 to 20,000 Da; (b) emulsifying the primary emulsion in an external water phase solution $W_2$ to obtain a $W_1/O/W_2$ double emulsion, wherein the ratio of $W_1/O$ is about is about 1:2 to 1:6 and wherein the $O/W_2$ ratio is about 1:1 to 1:6; (c) optionally diluting the $W_1/O/W_2$ double emulsion with an aqueous solution $W_3$ to form an optionally diluted $W_1/O/W_2$ double emulsion; and (d) removing the organic solvent from the optionally diluted $W_1/O/W_2$ double emulsion to form the bioactive or diagnostic agent loaded nanoparticles.

In yet another aspect, the method for preparing a bioactive or diagnostic agent loaded nanoparticles comprises the steps of (a) providing a $W_1$ solution comprising a bioactive agent or diagnostic agent in an aqueous solution; (b) providing an organic solution O comprising dichloromethane as an organic solvent and a polymer according to $PLA_z\text{-}PCL_y\text{-}PEG_x\text{-}PCL\text{-}PLA_z$ or $PGA_z\text{-}PCL_y\text{-}PEG_x\text{-}PCL_y\text{-}PGA_z$ or combinations thereof, wherein X defines an average molecular weight of 100 to 10,000 Da, wherein Y defines an average molecular weight of 500 to 20,000 Da, wherein Z defines an average molecular weight of 100 to 20,000 Da; (b) emulsifying the $W_1$ solution in the organic solution O to form a $W_1/O$ primary emulsion; (c) emulsifying the primary emulsion in an external water phase solution $W_2$ to obtain a $W_1/O/W_2$ double emulsion, wherein the ratio of $W_1/O$ is about 1:2 to 1:6 and wherein the $O/W_2$ ratio is about 1:1 to 1:6; (d) optionally diluting the $W_1/O/W_2$ double emulsion with an aqueous solution $W_3$ to form an optionally diluted $W_1/O/W_2$ double emulsion; and (e) isolating the bioactive or diagnostic agent loaded nanoparticles from the optionally diluted $W_1/O/W_2$ double emulsion.

In still another aspect, a method for improving or optimizing a loading of a bioactive agent or diagnostic agent in a polymer nanoparticulate formulation is provided. The method comprises the steps of (a) emulsifying a $W_1$ solution in an organic solution O to form a $W_1/O$ primary emulsion, wherein the $W_1$ solution comprises a bioactive agent or diagnostic agent in an aqueous solution, and the organic solution O comprises an organic solvent and a polymer; (b) emulsifying the primary emulsion in an external water phase solution $W_2$ to obtain a $W_1/O/W_2$ double emulsion; (c) optionally diluting the $W_1/O/W_2$ double emulsion with an aqueous solution $W_3$ to form an optionally diluted $W_1/O/W_2$ double emulsion; (d) removing the organic solvent from the optionally diluted $W_1/O/W_2$ double emulsion to form the bioactive agent or diagnostic agent loaded in a polymer nanoparticulate formulation; (e) measuring the loading of the bioactive agent or diagnostic agent in the nanoparticulate formulation; and repeating steps (a) to (e) while varying one or more parameters selected from: the molecular weight of the polymer, $W_1/O$ ratio (v/v), $O/W_2$ (v/v), $W_1/O/W_2$ (y/y/y), $W_1/W_2$ ratio (v/v), $W_1/W_3$ ratio (v/v), $W_2/W_3$ ratio (v/v), $W_1/(W_2+W_3)$, initial or nominal ratio of polymer to bioactive agent or diagnostic agent (w/w), and combinations thereof.

In some embodiments, the initial or nominal ratio of the polymer to the bioactive agent or diagnostic agent is about 10:1 to 2:1 (e.g., 10:1, 9:1, 8:1, 7:1, 6.1, 5:1, 4:1, 3:1, 2:1, or some range therebetween).

In certain embodiments, the $W_1/O$ ratio represents the ratio of the volume of the $W_1$ aqueous solution to the volume of the organic solution O. Typically, the $W_1/O$ ratio is about 1:2 to 1:6 (e.g., about 1:2, 1:3, 1:4, 1:5, 1:6, or some range therebetween).

In further embodiments, the $O/W_2$ ratio represents the ratio of the volume of the organic solution O to the volume of the external water phase solution $W_2$. Typically, the $O/W_2$ ratio is about 1:1 to 1:9 (e.g., about 1:1, 1:2, 1:3, 1:4, 1:5, 1:6, 1.7, 1.8, 1:9, or some range therebetween).

In some examples, the $W_1/O/W_2$ ratio represents the ratio of the volume of the $W_1$ aqueous solution to the volume of the organic solution O to the volume of the external water phase solution $W_2$. Preferably, the $W_1/O/W_2$ ratio is about 1:2:2 to 1:6:54 (e.g., about 1:2.5:4, 1:3:6, 1:3.5:7, 1:4:8, 1:4.5:15, 1:5:20, 1:6:36, 1:6:54 or some range therebetween.

In some embodiments, the $W_1/W_2$ ratio represents the ratio of the volume of $W_1$ aqueous solution to the volume of external water phase solution $W_2$. Typically, the $W_1/W_2$ ratio is about 1:2 to 1:54 (e.g., about 1:2, 1:3, 1:4, 1:5, 1:6, 1:7, 1:8, 1:9, 1:10, 1:11, 1:12, 1:13, 1:14, 1:15, 1:16, 1:7, 1:18, 1:19, 1:20, 1:21, 1:22, 1:23, 1:24, 1:25, 1:26, 1:27, 1:28, 1:29, 1:30, 1:31, 1:32, 1:33, 1:34, 1:35, 1:36, 1:37, 1:38, 1:39, 1:40, 1:41, 1:42, 1:43, 1:44, 1:45, 1:46, 1:47, 1:48, 1:49, 1:50, 1:51, 1:52, 1:53, 1:54, or some range therebetween).

In certain embodiments, the $W_1/(W_2+W_3)$ ratio represents the ratio of the volume of $W_1$ aqueous solution to the volume of the external water phase solution $W_2$ plus the dilution phase $W_3$. Typically, the $W_1/(W_2+W_3)$ ratio is about 1:20 to 1:100 (e.g., about 1:20, 1:30, 1:40, 1:50, 1:60, 1:70, 1:80, 1:90, 1:100 or some range therebetween). Preferably, the $W_1/(W_2+W_3)$ ratio is about 1:40 to about 1:60.

In some embodiments, the $W_1/W_3$ ratio represents the ratio of the volume of $W_1$ aqueous solution to the volume of the dilution phase $W_3$. Typically, the $W_1/W_3$ ratio is about 1:10 to about 1:80 (e.g., about 1:10, 1:15, 1:20, 1:25, 1:30, 1:35, 1:40, 1:45, 1:50, 1:55, 1:60, 1:65, 1:70, 1:75, 1:80 or some range therebetween).

In an embodiment, the $W_2/W_3$ ratio represents the ratio the volume of the external water phase solution $W_2$ to the volume of the dilution phase $W_3$. The $W_2/W_3$ ratio is about 1:1 to about 1:50 (e.g., about 1:1, 1:2, 1:3, 1:4, 1:5, 1:6, 1:7, 1:8, 1:9, 1:10, 1:15, 1:20, 1:25, 1:30, 1:35, 1:40, 1:45, 1:50 or some range therebetween).

The volatile organic solvent(s) used in the preparation of the nanoparticles by the double emulsion solvent evaporation method preferably have a low boiling point to facilitate the removal of residual solvent. Various water non-miscible solvents that can be used, including but not limited to dichloromethane, ethyl acetate, chloroform, benzene, alcohols, or combinations thereof.

The polymers of the nanoparticulate composition are biodegradable and biocompatible. In an exemplary embodiment, the nanoparticulate compositions are comprised of block polymers that form nanoparticles with a bioactive agent or diagnostic agent contained or otherwise encapsulated therein. The block polymers are preferably comprised of PEG, PCL, PGA, and/or PLA. Exemplary block polymers are pentablock polymers, such as those described in Mitra et al., U.S. Pat. No. 8,551,531, which is incorporated by reference. The pentablock polymers may be comprised of (1) PEG, (2) PCL, and (3) PGA or PLA. In one aspect, the block polymer is a pentablock polymer, i.e., a CBABC type block polymer. The pentablock polymer preferably has a configuration according to PGA-PCL-PEG-PCL-PGA, or PLA-PCL-PEG-PCL-PLA, or PCL-PLA-PEG-PLA-PCL, or PCL-PGA-PEG-PGA-PCL or combinations thereof.

In one aspect, the pentablock polymer may be defined according to:
$PLA_{100-20,000}$-$PCL_{500-20,000}$-$PEG_{100-10,000}$-$PCL_{500-20,000}$-$PLA_{100-20,000}$;
$PLA_{500-10,000}$-$PCL_{2500-15,000}$-$PEG_{500-7000}$-$PCL_{2500-15,000}$-$PLA_{500-10,000}$;
$PLA_{1000-5000}$-$PCL_{5000-10,000}$-$PEG_{2000-5000}$-$PCL_{5000-10,000}$-$PLA_{1000-5000}$; or
$PLA_{2000-4000}$-$PCL_{6000-8000}$-$PEG_{1000-6000}$-$PCL_{6000-8000}$-$PLA_{2000-4000}$.

In another aspect, the pentablock polymer may be defined according to:
$PGA_{100-20,000}$-$PCL_{500-20,000}$-$PEG_{100-10,000}$-$PCL_{500-20,000}$-$PGA_{100-20,000}$;
$PGA_{500-10,000}$-$PCL_{2500-15,000}$-$PEG_{500-7000}$-$PCL_{2500-15,000}$-$PGA_{500-10,000}$;
$PGA_{1000-5000}$-$PCL_{5000-10,000}$-$PEG_{2000-5000}$-$PCL_{5000-10,000}$-$PGA_{1000-5000}$; or
$PGA_{2000-4000}$-$PCL_{6000-8000}$-$PEG_{1000-6000}$-$PCL_{6000-8000}$-$PGA_{2000-4000}$.

In another aspect, the pentablock polymer may be defined according to:
$PGA_{100-5000}$-$PCL_{1000-20,000}$-$PEG_{200-20,000}$-$PCL_{1000-20,000}$-$PGA_{100-5000}$;
$PGA_{200-1000}$-$PCL_{2500-15,000}$-$PEG_{500-5000}$-$PCL_{2500-15,000}$-$PGA_{200-1000}$; or
$PGA_{200-800}$-$PCL_{5000-10,000}$-$PEG_{500-1500}$-$PCL_{5000-10,000}$-$PGA_{200-800}$.

In another aspect, the pentablock polymer may be a novel polymer of the present invention, as described above, including:
$PCL_{500-25,000}$-$PLA_{100-10,000}$-$PEG_{200-20,000}$-$PLA_{100-10,000}$-$PCL_{500-25,000}$;
$PCL_{500-25,000}$-$PGA_{100-15,000}$-$PEG_{200-20,000}$-$PGA_{100-15,000}$-$PCL_{500-25,000}$;
$PCL_{500-25,000}$-$PLA_{100-10,000}$-$PEG_{200-20,000}$-$PLA_{100-10,000}$-$PCL_{500-25,000}$; or
$PCL_{500-25,000}$-$PGA_{100-15,000}$-$PEG_{200-20,000}$-$PGA_{100-15,000}$-$PCL_{500-25,000}$ Bioactive Agents or Diagnostic Agents The pentablock polymers of the present invention are useful for encapsulating one or more bioactive agents or diagnostic agents for delivery. Examples of suitable bioactive agents or diagnostic agents include synthetic inorganic and organic compounds, proteins and peptides, polysaccharides and other sugars, lipids, gangliosides, and nucleic acid sequences having therapeutic or diagnostic activities. Nucleic acid sequences include genes, antisense molecules which bind to complementary DNA to inhibit transcription, and ribozymes. The agents to be incorporated can have a variety of biological activities, such as vasoactive agents, neuroactive agents, hormones, anticoagulants, immuno-modulating agents, cytotoxic agents, antibiotics, antivirals, antisense, antigens, and antibodies. Specific materials include antibiotics, antivirals, anti-inflammatories, both steroidal and non-steroidal, antineoplastics, anti-spasmodics including channel blockers, modulators of cell-extracellular matrix interactions including cell growth inhibitors and anti-adhesion molecules, enzymes and enzyme inhibitors, anticoagulants and/or antithrombotic agents, growth factors, DNA, RNA, inhibitors of DNA, RNA or protein synthesis, compounds modulating cell migration, proliferation and/or growth, vasodilating agents, and other drugs commonly used for the treatment of injury to tissue. Specific examples of these compounds include angiotensin converting enzyme inhibitors, prostacyclin, heparin, salicylates, nitrates, calcium channel blocking drugs, streptokinase, urokinase, tissue plasminogen activator ("TPA") and anisoylated plasminogen activator ("APA") and anisoylated plasminogen-streptokinase activator complex ("APSAC"), colchicine and alkylating agents, and aptamers. Specific examples of modulators of cell interactions include interleukins, platelet derived growth factor, acidic and basic fibroblast growth factor ("FGF"), transformation growth factor β ("TGF beta"), epidermal growth factor ("EGF"), insulin-like growth factor, and antibodies thereto. Specific examples of nucleic acids include genes and cDNAs encoding proteins, expression vectors, antisense and other oligonucleotides such as ribozymes which can be used to regulate or prevent gene expression. Specific examples of other bioactive agents include modified extracellular matrix components or their receptors, and lipid and cholesterol sequestrants. Typical anticancer agents include adriamycin, mitomycin, bleomycin, cisplatin, carboplatin, doxorubicin, daunorubicin, 5-fluorouracil, methotrexate, taxol, taxotere, actinomycin D, and the like. Exemplary diagnostic materials include paramagnetic molecules, fluorescent compounds, magnetic molecules, and radionuclides.

While not being specifically limited to the following, pharmaceutically useful polypeptides may be selected from group consisting of triamcinolone, acetonide, oxytocin, vasopressin, adrenocorticotrophic hormone, epidermal growth factor, platelet-derived growth factor ("PDGF"), prolactin, luliberin or luteinizing hormone releasing hormone, growth hormone, growth hormone releasing factor, insulin, somatostatin, glucagon, interleukin-2 ("IL-2"), interferon-alpha, beta, gamma, gastrin, tetragastrin, pentagastrin, urogastrone, secretin, calcitonin, enkephalins, endorphins, angiotensins, thyrotropin releasing hormone ("TRH"), tumor necrosis factor ("TNF"), nerve growth factor ("NGF"), granulocyte-colony stimulating factor ("G-CSF"), granulocyte macrophage-colony stimulating factor ("GM-CSF"), macrophage-colony stimulating factor ("M-CSF"), renin, bradykinin, bacitracins, polymixins, colistins, tyrocidine, gramicidines, monoclonal antibodies (e. g., IgG and the like), and synthetic analogues, modifications, and pharmacologically active fragments thereof, and soluble vaccines.

Specific examples of enzymes include aminopeptidase, alpha-amylase, amyloglucosidase, arabinofuranosidase, arabinoxylanase, beta-glucanase, carbohydrase, carboxypeptidase, catalase, cellobiohydrolase, cellulase, chitinase, cutinase, cyclodextrin glycosyltransferase, ferulic acid esterase, deoxyribonuclease, endo-cellulase, endo-glucanase, endo-xylanase, esterase, galactosidase, beta-galactosidase, glucoamylase, glucose oxidase, glucosidase, haloperoxidase, hemicellulase, invertase, isomerase, laccase, ligase, lipase, lyase, manannase, mannosidase, oxidase, pectate lyase, pectin lyase, pectin trans-eliminase, pectin ethylesterase, pectin methylesterase, pectinolytic enzyme, peroxidase, protease, phytase, phenoloxidase, polygalacturonase, polyphenoloxidase, proteolytic enzyme, rhamnogalacturonan lyase, rhamnoglucanase, rhamnogalacturonase, ribonuclease, SPS-ase, transferase, transglutaminase, xylanase and xyloglucanase.

Preferred bioactive agent or diagnostic agents include hydrophilic drugs, such as a peptides and proteins. The present invention is well adapted for the loading of highly hydrophilic drugs and particularly highly water-soluble peptide and protein drugs to the polymer nanoparticles. The drugs are released at a controlled rate with the corresponding biodegradation of the polymeric matrix.

The encapsulation of proteins in polymeric nanoparticles in accordance with the present invention generally involves a gentle emulsifying process. This is important so that the protein retains its tertiary/quaternary structure for biological activity. The process generally minimizes exposure to organic solvents, which tend to denature and render the proteins inactive.

The nanoparticulate compositions of the present invention may be administered to patient in need of treatment, along with a pharmaceutically acceptable carrier.

In some instances, physical stability of the bioactive agent or diagnostic agent with the pentablock polymers of the present invention can also be increased by various additives to aqueous solutions of the peptide or protein drugs. Additives, such as polyols (including sugars), amino acids, proteins such as collagen and gelatin, and certain salts may be used. These additives can readily be incorporated into the reverse thermal gelation compositions of the present invention.

Pentablock Nanoparticles in Pentablock Thermosensitive Gel

The pentablock polymers of the present invention may be dispersed in a thermosensitive gel. The thermosensitive gels are preferably pentablock polymers, such as those having a PEG-PCL-PLA-PCL-PEG configuration. Such polymers are described in Mitra et al., U.S. Pat. No. 8,851,531, which is incorporated by reference with respect to such disclosure. Thus, in another aspect, the present invention is directed to compositions of matter in which the pentablock nanoparticles having bioactive agent or diagnostic agent incorporated therein are dispersed the pentablock thermosensitive gel.

The pentablock polymer utilized for the preparation of thermosensitive gel is typically first dissolved in a pharmaceutically acceptable liquid, which is preferably a buffer. Preferably, the buffer comprises 10 mM phosphate buffer saline at 4° C. Typically, the concentration is about 5 to 75 wt % thermosensitive gelling pentablock polymer. Preferably, the concentration of the pentablock polymer is about 10 to 50 wt %, with about 20 wt % thermosensitive polymer solution being most preferred. After that, nanoparticles can be dispersed in the thermosensitive polymer solution to form a composite formulation comprised of nanoparticles suspended in the thermosensitive gel.

EXAMPLE 1

Synthesis of Pentablock Polymer for Nanoparticles

In this example, two pentablock polymers having a PCL-PLA-PEG-PLA-PCL block configuration were prepared. More specifically, the Pentablock Polymer E (PB-E) according to $PCL_{7000}$-$PLA_{3000}$-$PEG_{4000}$-$PLA_{3000}$-$PCL_{7000}$ and Pentablock Polymer F (PB-F) according to $PCL_{10000}$-

PLA$_{6000}$-PEG$_{4000}$-PLA$_{6000}$-PCL$_{10000}$ were prepared, wherein the subscript represents theoretical molecular weight of each block.

Pentablock Polymer E and Pentablock Polymer F were synthesized in two steps by sequential ring opening polymerization as shown in FIG. 1. Poly(ethylene glycol) was utilized as macroinitiator and stannous octoate as a catalyst. In the first step, triblock copolymer poly(lactide)-poly(ethylene glycol)-poly(lactide) (PLA-PEG-PLA) (Scheme 1) was synthesized by polymerization of L-lactide on two open hydroxyl ends of poly(ethylene glycol) (4000 Da). In brief, PEG was dissolved in anhydrous toluene followed by distillation to remove residual moisture. L-lactide and stannous octoate (0.5% w/w) were added to anhydrous PEG and temperature was raised to 150° C. After 24 h, reaction mixture (RM) was dissolved in methylene chloride followed by precipitation in cold petroleum ether. The precipitated polymer was filtered and dried for 24 h in vacuum at room temperature.

In the second step, the PLA-PEG-PLA triblock copolymer was reacted with ε-caprolactone to prepare the PB copolymer (Scheme 2, PB-E and PB-F). The triblock copolymer and ε-caprolactone were added in round bottom flask and temperature was raised to 150° C. under inert atmosphere. To this, stannous octoate (0.5% w/w) was added as a catalyst and reaction was allowed to run for 24 h. The pentablock copolymer was purified by cold ether precipitation method described in the first step. The polymer was dried under vacuum and stored at −20° C. until further use.

Figure 2:
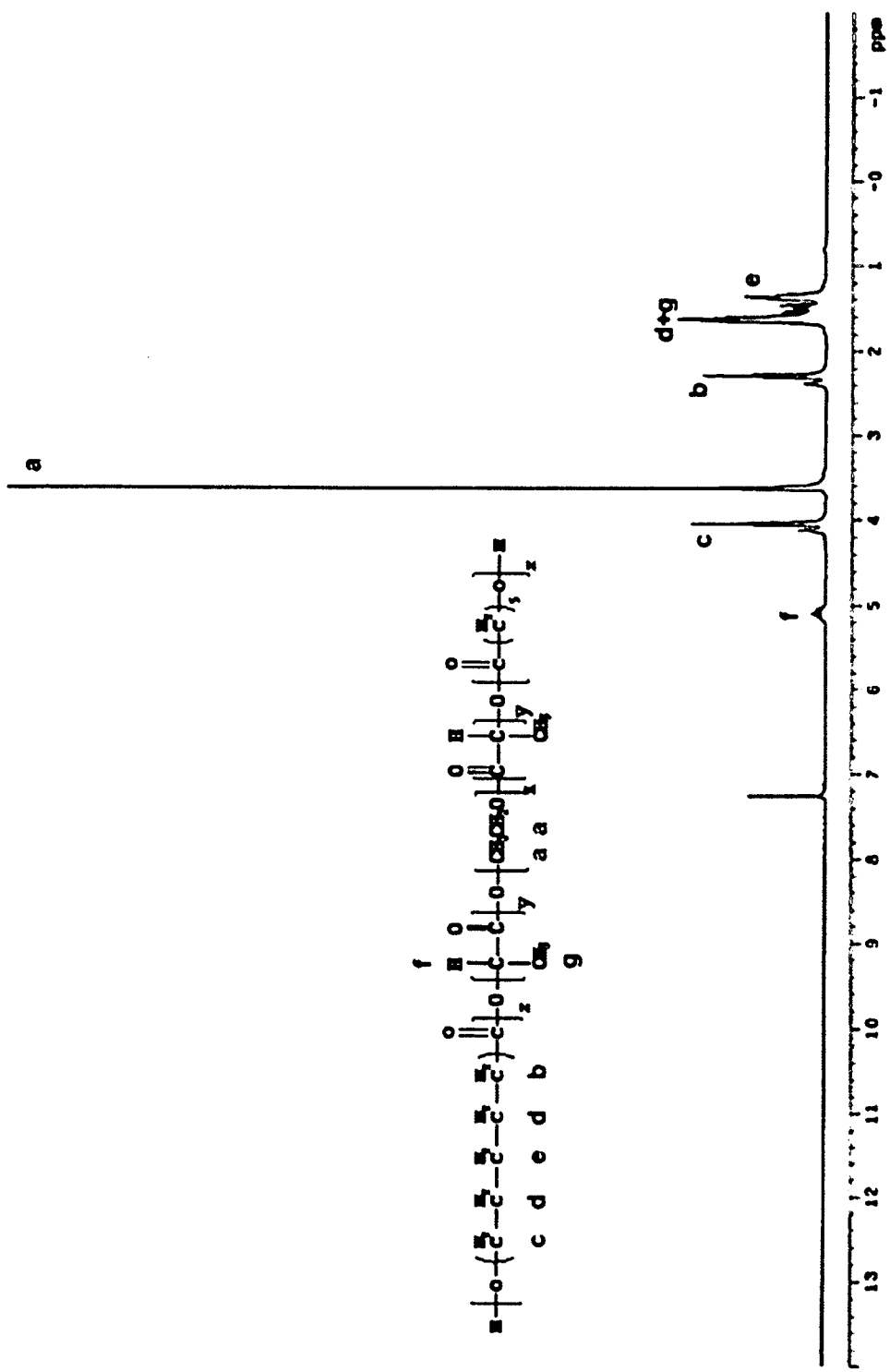
FIG. 2 shows the $^1$H-NMR spectra of Pentablock Polymer E.
Figure 3:
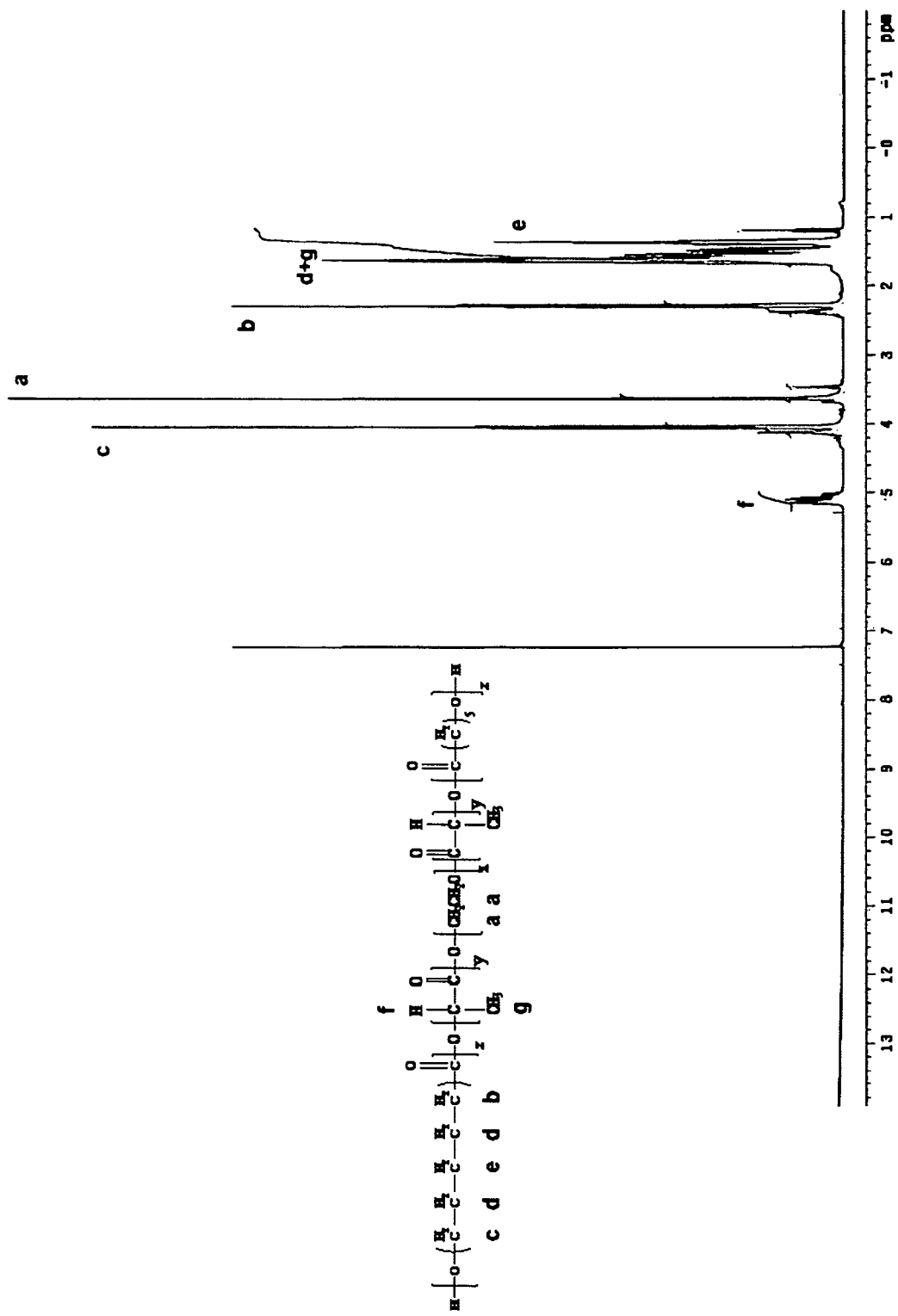
FIG. 3 shows the $^1$H-NMR spectra of Pentablock Polymer F.

The resulting polymers were characterized for molecular weight and purity by $^1$H NMR spectroscopy. Polymeric materials were dissolved in CDCl$_3$ and spectrograms were recorded with Varian-400 NMR instrument. The results are shown in FIG. 2 and FIG. 3.

EXAMPLE 2

Synthesis of Pentablock Polymer

Figure 4:
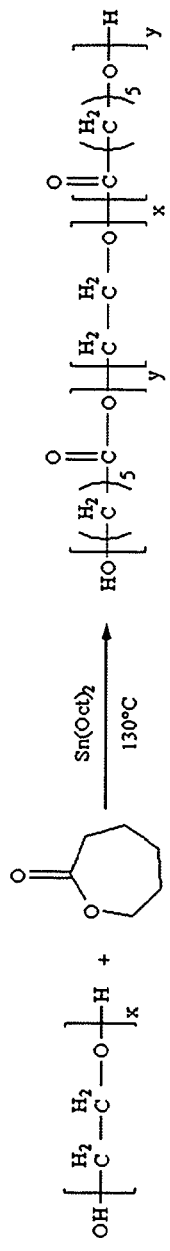
FIG. 4 is an exemplary scheme for synthesizing pentablock polymers for use in the nanoparticulate compositions of the present invention.
Figure 4:
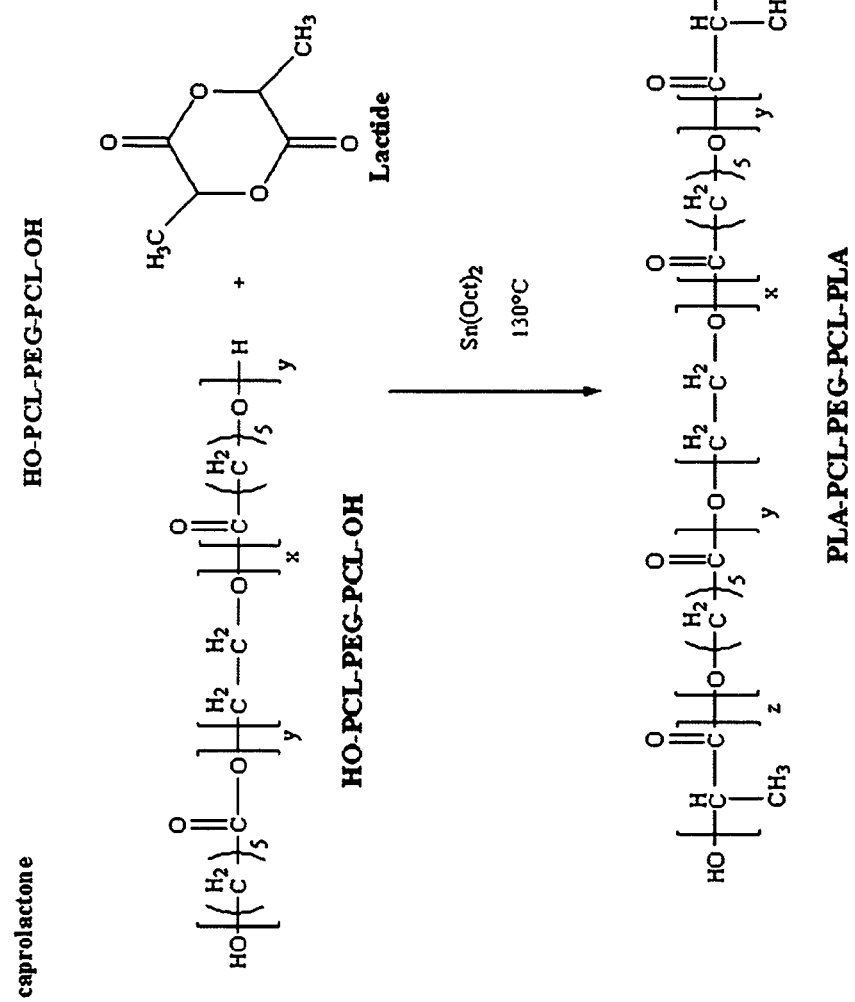

Poly(lactide)-poly(caprolactone)-poly(ethylene glycol)-poly(caprolactone)-poly(lactide) (PLA-PCL-PEG-PCL-PLA) block copolymers were synthesized by ring opening polymerization method. Pentablock copolymers ("PB") with compositions PLA$_{3000}$-PCL$_{7000}$-PEG$_{2000}$-PCL$_{7000}$-PLA$_{3000}$ ("PB-A") and PLA$_{3000}$-PCL$_{7000}$-PEG$_{4000}$-PCL$_{7000}$-PLA$_{3000}$ ("PB-B") were synthesized. The subscript in polymer composition represents theoretical molecular weight of each block. PB copolymers were prepared in two steps by sequential ring opening polymerization. In the first step, ε-caprolactone was polymerized on poly(ethylene glycol) of molecular weight 2000 or 4000 Da in presence of stannous octoate as a catalyst to form the triblock copolymer poly(caprolactone)-poly(ethylene glycol)-poly(caprolactone) (PCL-PEG-PCL) (FIG. R, Scheme 1). In brief, PEG was dissolved in anhydrous toluene followed by distillation to remove residual moisture. ε-caprolactone and stannous octoate (0.5% w/w of reactant concentration) were added to anhydrous PEG and temperature was raised to 130° C. After 24 hours, the degassed (30 minutes) reaction mixture ("RM") was dissolved in methylene chloride followed by precipitation in cold petroleum ether. The precipitated polymer was filtered and dried for 24 hours in vacuum at room temperature. The scheme is illustrated in FIG. 4.

Figure 5A:
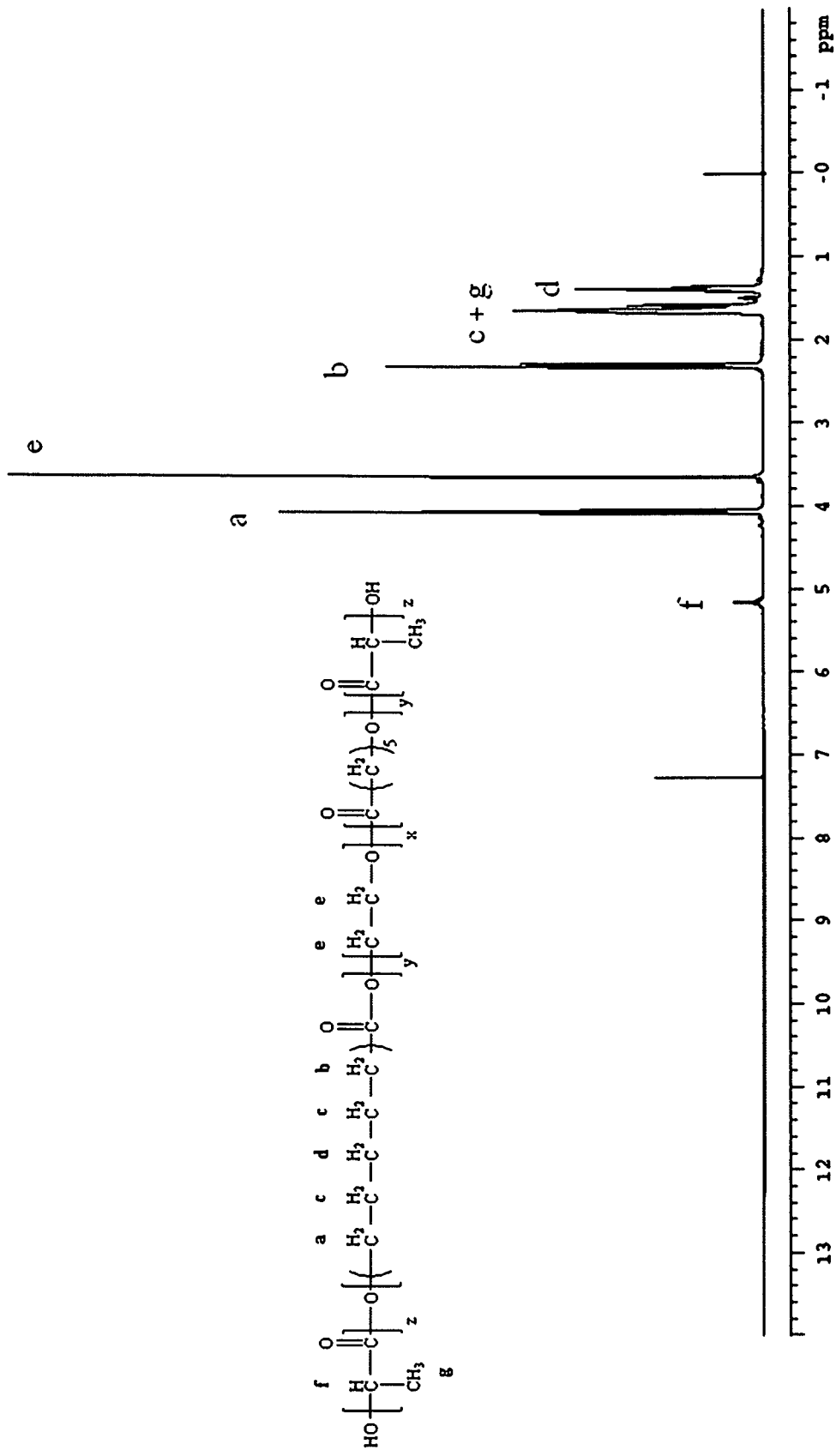
FIGS. 5A and 5B are the 1H NMR spectroscopy for the pentablock polymers of FIG. 4.
Figure 5B:
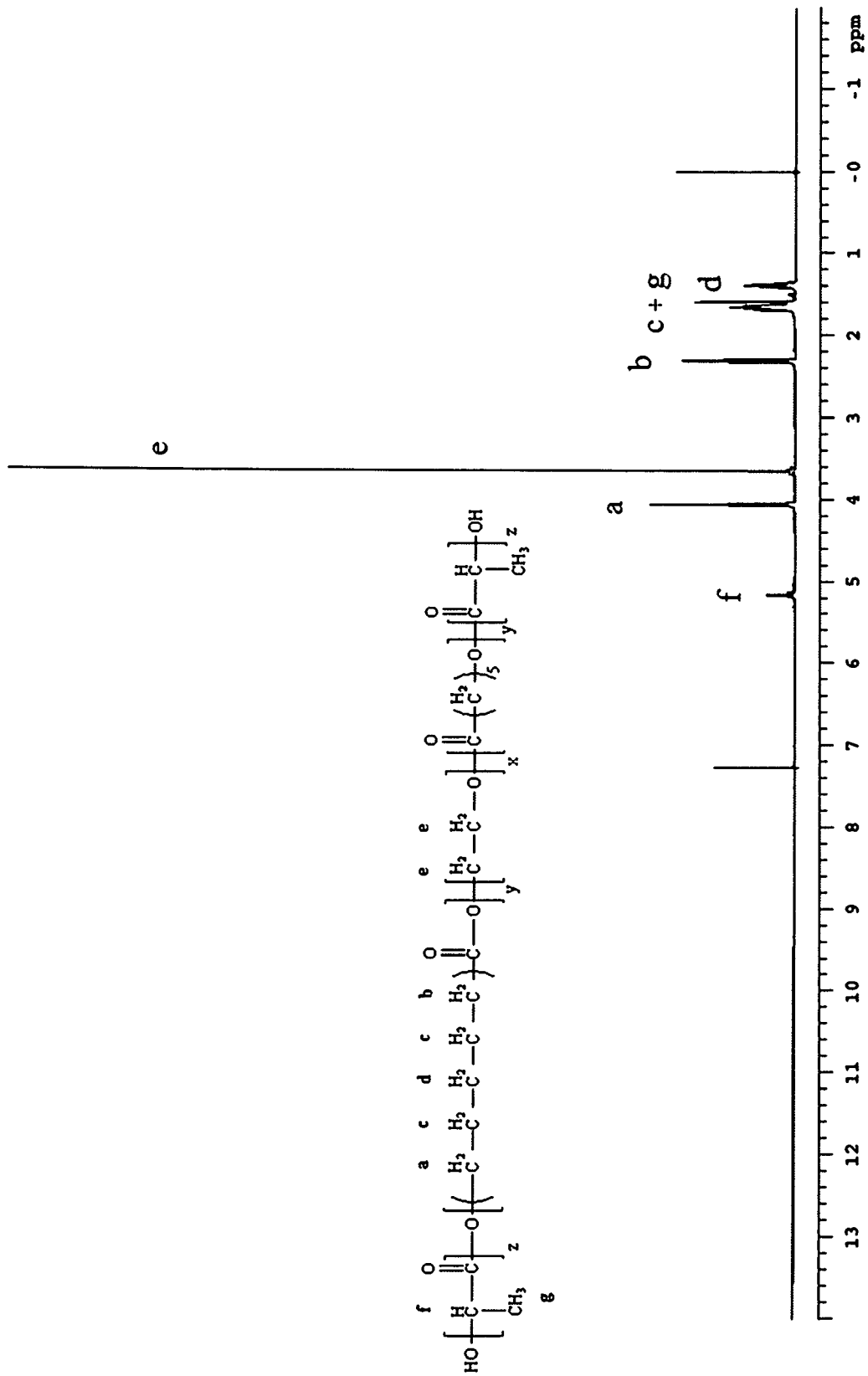

The polymer compositions were characterized by 1H NMR spectroscopy. Spectra were recorded by dissolving polymeric material in CDCl3 with Varian-400 NMR instrument. The results are shown in FIGS. 5A and 5B.

EXAMPLE 3

Nanoparticle Preparation Method

Protein/peptide-loaded pentablock ("PB") nanoparticles ("NPs") may be prepared by W$_1$/O/W$_2$ double emulsion solvent evaporation method. Briefly, in one exemplary embodiment of the method, an organic phase (e.g. dichloromethane) containing dissolved pentablock polymer is prepared. A peptide/protein containing aqueous solution (W$_1$ phase) is emulsified in the organic phase using probe sonication for 30 seconds to form W$_1$/O primary emulsion. The primary emulsion is further emulsified in water phase containing 2% polyvinyl alcohol (PVA) using probe sonication for 30 seconds to obtain W$_1$/O/W$_2$ double emulsion. The resulting double emulsion is further diluted with 2% PVA (W$_3$) under continuous stirring. The organic phase in the diluted emulsion is then evaporated under vacuum, preferably using rotavap, to obtain NPs. The NPs are separated by ultracentrifugation at 20,000 rpm for 30 minutes. The particles are washed twice with distilled deionized water ("DDW") and centrifuged to remove traces of PVA and unentrapped peptide/protein. Purified NPs are freeze dried with mannitol (5% w/v) and stored at −20° C. until further use.

Detailed process parameters for exemplary peptide/proteins and pentablock nanoparticles are described in the following Examples. Process parameters such as phase volume ratio, drug:polymer ratio, and types of polymer were optimized to achieve higher drug loading.

Nanoparticles may be characterized for entrapment efficiency, drug loading and in vitro release behavior.

Entrapment Efficiency and Drug Loading:

Amount of unentrapped protein/peptide in supernatant may be determined by micro BCA™ protein assay kit following manufacturer's protocol.

Entrapment efficiency (% EE) was calculated with eq. 1:

$$\% \, EE = \left(1 - \frac{\text{Amount of drug in supernatant}}{\text{Total amount of drug}}\right) * 100 \qquad \text{eq. 1}$$

Amount of entrapped protein/peptide in nanoparticles may be determined by UV spectroscopy.

Drug loading (% DL) may be calculated by eq. 2:

$$\% \, DL = \left(\frac{\text{Amount of drug in nanoparticles}}{\text{Total amount of drug and polymer}}\right) * 100 \qquad \text{eq. 2}$$

It will be appreciated to those skilled in the art that the total amount of drug and polymer in the denominator of the DL refers the actual weight, which is experimentally derived.

EXAMPLE 3A

IgG-Fab-Loaded Nanoparticles

IgG-Fab is a fragment of IgG with molecular weight of 48 kDa. In order to achieve high IgG-Fab loading, effects of various process parameters such as phase volume ratio, drug:polymer ratio and types of polymer were examined.

Two PB copolymers with different hydrophobicity were synthesized and characterized, namely, PB-A and PB-B, where PB-A is more hydrophobic polymer relative to PB-B polymer.

Nanoparticles composed of PB copolymers were formulated by previously described $W_1/O/W_2$ double emulsion solvent evaporation method. The details of process parameters and results are given in Table 1. IgG-Fab-loaded NPs were prepared utilizing both PB copolymers to determine the effect of polymer type on drug loading. As represented in Table 1, drug loadings were 5.62% and 4.99% for Batches 1 and 2, respectively. NPs composed of PB-A polymer (Batch 1) demonstrated higher drug loading relative to PB-B NPs (Batch 2), which may be attributed to relatively high hydrophobicity of PB-A polymer. During solvent evaporation, high hydrophobicity may allow faster polymer precipitation to form NPs preventing diffusion of IgG-Fab in external aqueous ($W_2$) phase. Based on the results from Batches 1 and 2, PB-A polymer was used for further NPs optimization.

In order to further enhance drug loading, drug:polymer ratio was increased from 1:10 (Batches 1 and 2) to 1:4 (Batch 3). Despite of high drug:polymer ratio with Batch 3, there was no significant difference observed in drug loading compared to earlier PB-A NPs Batch 1. The poor drug loading could be attributed to high volume of external aqueous ($W_2$) phase. Hence, in further studies drug:polymer ratio was kept constant at 1:4 and effect of external phase ($W_2$) volume was evaluated. For instance, in Batch 4 total external phase ($W_2$) volume was lowered to 5 ml. In addition, double emulsion was prepared with 2 ml of external aqueous ($W_2$) phase to reduce partition of protein in water ($W_2$ phase). The resulting multiple emulsion was stabilized by dilution with 3 ml of 2% PVA ($W_3$ phase). Interestingly, 11.7% of drug loading was observed with Batch 4 which was significantly higher compared to all earlier batches.

Based on results from Batch 4, it can be inferred that reduction in external phase ($W_2$) volume along with high drug:polymer ratio have significant effect on drug loading. Hence, volumes of all the phases were further lowered while keeping the volume ratio constant. It was hypothesized that the lower volume of $W_2$ would diminish partition of protein in aqueous phase improving loading efficiency. In addition, reduction in organic phase volume would increase polymer concentration that may lead to faster polymer precipitation and NPs formation. A drug loading of 15.61% was observed with NPs in Batch 5 as expected. However, further reduction in volumes did not result in any improvement in drug loading (15.47%) with Batch 6 (Table 1).

EXAMPLE 3B

Drug Encapsulation in Pentablock Polymeric Nanoparticles

In this example, IgG-Fab-encapsulated nanoparticles with various pentablock copolymers were prepared. Nanoparticles composed of pentablock copolymers were prepared by the $W_1/O/W_2$ double emulsion solvent evaporation method described above. Briefly, an aqueous solution of IgG-Fab ($W_1$ phase) was added drop-wise in an organic phase (containing pentablock polymer dissolved in methylene chloride) under constant sonication (2 Watt output, 30 seconds). The resulting primary emulsion ($W_1/O$) was then added drop-wise in $W_2$ phase (2% PVA) under constant sonication (2 Watt output, 45 seconds). The resulting double emulsion ($W_1/O/W_2$) was diluted in $W_3$ phase (2% PVA) [under continuous stirring] followed by evaporation of methylene chloride at low pressure. After evaporation, nanoparticles were centrifuged for 30 min at 20,000 rpm (4° C.). The nanoparticles were then washed two times with distilled deionized water and centrifuged. The final pellet of nanoparticle was suspended in mannitol solution (1.5%/3%). Nanoparticles were freeze-dried overnight and stored at −20° C. until further use. Nanoparticles were characterized for entrapment efficiency, drug loading and in vitro release behavior.

The different pentablock polymer sequences tested included those described in Mitra et al., U.S. Pat. No. 8,851,531, which is incorporated by reference, as well as the new pentablock polymers described herein.

Pentablock Polymer A (PB-A): $PLA_{3000}\text{-}PCL_{7000}\text{-}PEG_{2000}\text{-}PCL_{7000}\text{-}PLA_{3000}$ Pentablock Polymer B (PB-B): $PLA_{3000}\text{-}PCL_{7000}\text{-}PEG_{4000}\text{-}PCL_{7000}\text{-}PLA_{3000}$ Pentablock Polymer C (PB-C): $PGA_{3000}\text{-}PCL_{7000}\text{-}PEG_{4000}\text{-}PCL_{7000}\text{-}PGA_{3000}$ Pentablock Polymer D (PB-D): $PGA_{3000}\text{-}PCL_{7000}\text{-}PEG_{2000}\text{-}PCL_{7000}\text{-}PGA_{3000}$ Pentablock Polymer E (PB-E): $PCL_{7000}\text{-}PLA_{3000}\text{-}PEG_{4000}\text{-}PLA_{3000}\text{-}PCL_{7000}$ Pentablock Polymer F (PB-F): $PCL_{10000}\text{-}PLA_{6000}\text{-}PEG_{4000}\text{-}PLA_{6000}\text{-}PCL_{10000}$ The details of process parameters and results are given in Table 2.

TABLE 1

Optimization of process parameters for the IgG-Fab-loaded NPs

| Batch # | Polymer Types | Polymer Amount (mg) | Amount of IgG-Fab (mg) | Volume of $W_1$ (mL) | Volume of organic phase (mL) | Volume of $W_2$ (mL) | Volume of $W_3$ (mL) | EE (%) | Drug loading (%) |
|---|---|---|---|---|---|---|---|---|---|
| Batch 1 | PB-A | 100 | 10  | 1     | 4     | 20    | —     | 54.03 ± 1.80 | 5.62 ± 0.20 |
| Batch 2 | PB-B | 100 | 10  | 1     | 4     | 20    | —     | 45.72 ± 2.65 | 4.99 ± 0.29 |
| Batch 3 | PB-A | 10  | 2.5 | 0.25  | 1     | 8.8   | —     | 25.85 ± 2.25 | 6.4 ± 1.04 |
| Batch 4 | PB-A | 10  | 2.5 | 0.25  | 1     | 2     | 3     | 45.23 ± 1.58 | 11.7 ± 1.26 |
| Batch 5 | PB-A | 10  | 2.5 | 0.167 | 0.667 | 1.333 | 3.667 | 69.64 ± 9.01 | 15.61 ± 1.97 |
| Batch 6 | PB-A | 10  | 2.5 | 0.1   | 0.4   | 0.8   | 4.2   | 73.24 ± 0.20 | 15.47 ± 0.04 |

TABLE 2

Process parameters of the IgG-Fab-loaded PB NPs

| Batch # | Polymer types | Polymer Amount (mg) | Amount protein/ peptide (mg) | Volume of $W_1$ (mL) | Volume oil phase (mL) | Volume of $W_2$ (mL) | Volume of $W_3$ (mL) | EE (%) | Drug loading (%) |
|---|---|---|---|---|---|---|---|---|---|
| Batch 6 | PB-A | 10 | 2.5 | 0.1 | 0.4 | 0.8 | 4.2 | 73.24 ± 0.20 | 15.47 ± 0.04 |
| Batch 18 | PB-C | 10 | 2.5 | 0.1 | 0.4 | 0.8 | 4.2 | 57.15 ± 8.49 | 12.49 ± 1.62 |
| Batch 20 | PB-D | 10 | 2.5 | 0.1 | 0.4 | 0.8 | 4.2 | 78.09 ± 0.44 | 16.34 ± 0.08 |
| Batch 29 | PB-E | 9 | 3 | 0.1 | 0.4 | 0.8 | 4.2 | 42.91 ± 0.30 | 9.69 ± 0.06 |
| Batch 30 | PB-F | 9 | 3 | 0.1 | 0.4 | 0.8 | 4.2 | 68.05 ± 2.01 | 18.49 ± 0.45 |

IgG-Fab-loaded nanoparticles were prepared utilizing both Pentablock Polymer E and Pentablock Polymer F copolymers to determine the effect of polymer type on drug loading. As represented in Table 2, drug loading observed were 9.69% and 18.49% for PB-E and PB-F, respectively. Significantly higher drug loading was observed with PB-F nanoparticles relative to PB-E nanoparticles, which may be attributed to relatively high hydrophobicity of PB-F copolymer. During solvent evaporation, high hydrophobicity may allow faster polymer precipitation to form nanoparticles preventing diffusion of IgG-Fab in external aqueous ($W_2$) phase.

EXAMPLE 3C

IgG-Loaded Nanoparticles

IgG is a full length human antibody with molecular weight of 150 kDa. IgG-loaded NPs were also prepared with PB-A polymer using optimal process parameters from Batches 5 and 6. The results for IgG-loaded NPs are represented in Table 3. A drug loading of only 12% was observed in Batch 8 NPs. Despite the high volumes of all phases relative to Batch 8, a higher drug loading of 15.71% was obtained with Batch 7 NPs (Table 3).

TABLE 3

Optimization of process parameters for the IgG-loaded NPs

| | | | | Process parameters | | | | | |
| Batch # | Polymer types | Polymer Amount (mg) | Amount of IgG (mg) | Volume of $W_1$ (mL) | Volume of organic phase (mL) | Volume of $W_2$ (mL) | Volume of $W_3$ (mL) | EE (%) | Drug loading (%) |
|---|---|---|---|---|---|---|---|---|---|
| Batch 7 | PB-A | 10 | 2.5 | 0.167 | 0.667 | 1.333 | 3.667 | 74.57 ± 1.31 | 15.71 ± 0.23 |
| Batch 8 | PB-A | 10 | 2.5 | 0.1 | 0.4 | 0.8 | 4.2 | 54.56 ± 2.56 | 12.00 ± 0.49 |

EXAMPLE 3D

Catalase-Loaded Nanoparticles

To determine the applicability of optimized novel process parameters to encapsulate proteins larger than antibodies, catalase was used as model protein. Catalase is a hydrogen peroxidase degrading enzyme with molecular weight of 240 kDa. Catalase-loaded PB NPs were prepared according to optimized process parameters mentioned in Batches 5 and 6. A significantly high protein loading of 16.43% and 16.12% were observed in Batches 15 and 16, respectively (Table 4). The result also suggested that the further reduction in phase volumes did not produce significant effect in protein loading.

TABLE 4

Optimization of process parameters for the catalase-loaded NPs

| | | | | Process parameters | | | | | |
| Batch # | Polymer types | Polymer Amount (mg) | Amount of catalase (mg) | Volume of $W_1$ (mL) | Volume of organic phase (mL) | Volume of $W_2$ (mL) | Volume of $W_3$ (mL) | EE (%) | Drug loading (%) |
|---|---|---|---|---|---|---|---|---|---|
| Batch 15 | PB-A | 10 | 2.5 | 0.167 | 0.667 | 1.333 | 3.667 | 78.64 ± 0.81 | 16.43 ± 0.14 |
| Batch 16 | PB-A | 10 | 2.5 | 0.1 | 0.4 | 0.8 | 4.2 | 76.87 ± 0.58 | 16.12 ± 0.10 |

EXAMPLE 3E

Loading of Low Molecular Weight Peptides/Proteins in PB NPs

The applicability of PB copolymer was further evaluated for the delivery of low molecular weight proteins and peptides ranging from 1 kDa to 15 kDa. The optimal process parameter obtained from Batches 5 and 6 were utilized to prepare lysozyme (14.7 kDa), insulin (5.8 kDa) and octreotide (1 kDa) loaded NPs.

Loading efficiencies for lysozyme, insulin, and octreotide loaded NPs are illustrated in Tables 5, 6, and 7, respectively.

The drug loading of 6-9% was observed with all the proteins/peptides mentioned above (Batches 9-14). Interestingly, loading efficiencies for low molecular weight peptides and proteins were inherently less than high molecular weight proteins like IgG-Fab, IgG, and catalase. The probable reason could be the lower molecular weight of these agents which may allow faster diffusion into the external aqueous phase. These results clearly suggest that molecular weight of proteins/peptides have significant effect on drug loading. For further clarification, volumes of $W_1$, $W_2$, $W_3$ and 0 phases along with their ratios are described in Table 8. Protein and peptide-loaded PB NPs (Batches 5-16) were also characterized for particle size and polydispersity (Table 9). Results demonstrated that all the PB NPs were well below the 1 μm of particle size (ranging from 220-910 nm) with polydispersity ranging between 0.175-0.660.

TABLE 5

Optimization of process parameters for the lysozyme-loaded NPs

| Batch # | Polymer types | Polymer Amount (mg) | Amount of lysozyme (mg) | Volume of $W_1$ (mL) | Volume of organic phase (mL) | Volume of $W_2$ (mL) | Volume of $W_3$ (mL) | EE (%) | Drug loading (%) |
|---|---|---|---|---|---|---|---|---|---|
| Batch 9 | PB-A | 10 | 2.5 | 0.167 | 0.667 | 1.333 | 3.667 | 37.64 ± 1.66 | 8.60 ± 0.35 |
| Batch 10 | PB-A | 10 | 2.5 | 0.1 | 0.4 | 0.8 | 4.2 | 38.44 ± 2.44 | 8.77 ± 0.51 |

TABLE 6

Optimization of process parameters for the insulin-loaded NPs

| Batch # | Polymer types | Polymer Amount (mg) | Amount of insulin (mg) | Volume of $W_1$ (mL) | Volume of organic phase (mL) | Volume of $W_2$ (mL) | Volume of $W_3$ (mL) | EE (%) | Drug loading (%) |
|---|---|---|---|---|---|---|---|---|---|
| Batch 11 | PB-A | 10 | 2.5 | 0.167 | 0.667 | 1.333 | 3.667 | 38.41 ± 0.75 | 8.76 ± 0.15 |
| Batch 12 | PB-A | 10 | 2.5 | 0.1 | 0.4 | 0.8 | 4.2 | 36.39 ± 2.29 | 8.34 ± 0.48 |

TABLE 7

Optimization of process parameters for the octreotide-loaded NPs

| Batch # | Polymer types | Polymer Amount (mg) | Amount of octreotide (mg) | Volume of $W_1$ (mL) | Volume of organic phase (mL) | Volume of $W_2$ (mL) | Volume of $W_3$ (mL) | EE (%) | Drug loading (%) |
|---|---|---|---|---|---|---|---|---|---|
| Batch 13 | PB-A | 10 | 2.5 | 0.167 | 0.667 | 1.333 | 3.667 | 35.79 ± 3.63 | 8.20 ± 0.77 |
| Batch 14 | PB-A | 10 | 2.5 | 0.1 | 0.4 | 0.8 | 4.2 | 26.88 ± 1.56 | 6.30 ± 0.34 |

TABLE 8

Volume ratios of $W_1/O/W_2$

| Batch # | Type of protein/ peptide | Volume of $W_1$ (mL) | Volume of organic phase (mL) | Volume of $W_2$ (mL) | Volume of $W_3$ (mL) | Phase volume ratios ($W_1/O/W_2$) | EE % | Loading % |
|---|---|---|---|---|---|---|---|---|
| Batch 1 | IgG-Fab | 1 | 4 | 20 | — | 1:4:20 | 54.03 ± 1.80 | 5.62 ± 0.20 |
| Batch 2 | IgG-Fab | 1 | 4 | 20 | — | 1:4:20 | 45.72 ± 2.65 | 4.99 ± 0.29 |
| Batch 3 | IgG-Fab | 0.25 | 1 | 8.8 | — | 1:4:35.2 | 25.85 ± 2.25 | 6.4 ± 1.04 |
| Batch 4 | IgG-Fab | 0.25 | 1 | 2 | 3 | 1:4:8 | 45.23 ± 1.58 | 11.7 ± 1.26 |

TABLE 8-continued

Volume ratios of $W_1/O/W_2$

| Batch # | Type of protein/ peptide | Volume of $W_1$ (mL) | Volume of organic phase (mL) | Volume of $W_2$ (mL) | Volume of $W_3$ (mL) | Phase volume ratios ($W_1/O/W_2$) | EE % | Loading % |
|---|---|---|---|---|---|---|---|---|
| Batch 5 | IgG-Fab | 0.167 | 0.667 | 1.333 | 3.667 | 1:4:8 | 69.64 ± 9.01 | 15.61 ± 1.97 |
| Batch 6 | IgG-Fab | 0.1 | 0.4 | 0.8 | 4.2 | 1:4:8 | 73.24 ± 0.20 | 15.47 ± 0.04 |
| Batch 7 | IgG | 0.167 | 0.667 | 1.333 | 3.667 | 1:4:8 | 74.57 ± 1.31 | 15.71 ± 0.23 |
| Batch 8 | IgG | 0.1 | 0.4 | 0.8 | 4.2 | 1:4:8 | 54.56 ± 2.56 | 12.00 ± 0.49 |
| Batch 9 | Lysozyme | 0.167 | 0.667 | 1.333 | 3.667 | 1:4:8 | 37.64 ± 1.66 | 8.60 ± 0.35 |
| Batch 10 | Lysozyme | 0.1 | 0.4 | 0.8 | 4.2 | 1:4:8 | 38.44 ± 2.44 | 8.77 ± 0.51 |
| Batch 11 | Insulin | 0.167 | 0.667 | 1.333 | 3.667 | 1:4:8 | 38.41 ± 0.75 | 8.76 ± 0.15 |
| Batch 12 | Insulin | 0.1 | 0.4 | 0.8 | 4.2 | 1:4:8 | 36.39 ± 2.29 | 8.34 ± 0.48 |
| Batch 13 | Octreotide | 0.167 | 0.667 | 1.333 | 3.667 | 1:4:8 | 35.79 ± 3.63 | 8.20 ± 0.77 |
| Batch 14 | Octreotide | 0.1 | 0.4 | 0.8 | 4.2 | 1:4:8 | 26.88 ± 1.56 | 6.30 ± 0.34 |
| Batch 15 | Catalase | 0.167 | 0.667 | 1.333 | 3.667 | 1:4:8 | 78.64 ± 0.81 | 16.43 ± 0.14 |
| Batch 16 | Catalase | 0.1 | 0.4 | 0.8 | 4.2 | 1:4:8 | 76.87 ± 0.58 | 16.12 ± 0.10 |

Note:
Between Batches 4 to 16, volume of $W_3$ was adjusted in such a way that total volume of external phase ($W_2 + W_3$) sums up to 5 mL.

TABLE 9

Particle size and polydispersity of nanoparticles prepared with optimized parameters

| Batch # | Protein/peptide | Particle size (nm) | Polydispersity Index |
|---|---|---|---|
| Batch 5 | IgG-Fab | 470.8 | 0.552 |
| Batch 6 | IgG-Fab | 643.5 | 0.530 |
| Batch 7 | IgG | 475.0 | 0.18 |
| Batch 8 | IgG | 605.4 | 0.658 |
| Batch 9 | Lysozyme | 342.3 | 0.306 |
| Batch 10 | Lysozyme | 363.1 | 0.281 |
| Batch 11 | Insulin | 261.4 | 0.293 |
| Batch 12 | Insulin | 237.2 | 0.188 |
| Batch 13 | Octreotide | 235.7 | 0.194 |
| Batch 14 | Octreotide | 220.4 | 0.178 |
| Batch 15 | Catalase | 907.4 | 0.646 |
| Batch 16 | Catalase | 811.5 | 0.221 |

EXAMPLE 4

Protein/Peptide Loaded PB NP

In this example, the development of nanoparticles with glycolide (PGA) based PB copolymers is demonstrated to achieve high loading of large proteins and peptides. Two glycolide-based PB copolymers with different hydrophobicity were synthesized and characterized, namely PB-D and PB-C. PB-D is a more hydrophobic copolymer relative to PB-C.

$W_1/O/W_2$ methods optimized earlier for PB-A copolymer (Batches 5 and 6) were utilized for PB-C and PB-D copolymers. As shown in Table 10, mean drug loading for IgG-Fab was 10.49 and 12.49% (Batches 17 & 18) with PB-C. However, loading of IgG-Fab with PB-D was 17.19 and 16.34% (Batches 19 & 20), which was significantly higher relative to PB-C copolymer. The higher loading efficiency may be due to hydrophobic nature of the PB-D copolymer. A similar trend in drug loading is observed for IgG-loaded NPs. There was a small increase in drug loading with PB-D compare to PB-C copolymer (Batches 21-24). With catalase, a 240 kDa protein, drug loading efficiency remains relatively similar for both PB-C and PB-D NPs prepared by either method (Batches 25-28). Overall, as the protein molecular weight is increasing from 48 kDa to 240 kDa, the difference in drug loading for PB-C and PB-D is reducing. This may be due to the decreased diffusivity of protein with increased molecular weight.

TABLE 10

Optimization of process parameters for the protein-loaded NPs

| Batch # | Type of protein/ peptide | Polymer types | Polymer Amount (mg) | Amount protein/ peptide (mg) | Volume of $W_1$ (mL) | Volume oil phase (mL) | Volume of $W_2$ (mL) | Volume of $W_3$ (mL) | EE (%) | Drug loading (%) |
|---|---|---|---|---|---|---|---|---|---|---|
| Batch 17 | IgG-Fab | PB-C | 10 | 2.5 | 0.167 | 0.667 | 1.333 | 3.667 | 46.87 ± 0.84 | 10.49 ± 0.17 |
| Batch 18 | IgG-Fab | PB-C | 10 | 2.5 | 0.1 | 0.4 | 0.8 | 4.2 | 57.15 ± 8.49 | 12.49 ± 1.62 |
| Batch 19 | IgG-Fab | PB-D | 10 | 2.5 | 0.167 | 0.667 | 1.333 | 3.667 | 83.09 ± 1.44 | 17.19 ± 0.25 |
| Batch 20 | IgG-Fab | PB-D | 10 | 2.5 | 0.1 | 0.4 | 0.8 | 4.2 | 78.09 ± 0.44 | 16.34 ± 0.08 |
| Batch 21 | IgG | PB-C | 10 | 2.5 | 0.167 | 0.667 | 1.333 | 3.667 | 72.02 ± 0.71 | 15.26 ± 0.13 |
| Batch 22 | IgG | PB-C | 10 | 2.5 | 0.1 | 0.4 | 0.8 | 4.2 | 68.54 ± 1.42 | 14.63 ± 0.26 |
| Batch 23 | IgG | PB-D | 10 | 2.5 | 0.167 | 0.667 | 1.333 | 3.667 | 85.31 ± 0.4 | 17.58 ± 0.07 |
| Batch 24 | IgG | PB-D | 10 | 2.5 | 0.1 | 0.4 | 0.8 | 4.2 | 81.77 ± 0.63 | 16.97 ± 0.11 |
| Batch 25 | Catalase | PB-C | 10 | 2.5 | 0.167 | 0.667 | 1.333 | 3.667 | 75.84 ± 1.19 | 15.94 ± 0.21 |
| Batch 26 | Catalase | PB-C | 10 | 2.5 | 0.1 | 0.4 | 0.8 | 4.2 | 72.08 ± 0.68 | 15.27 ± 0.12 |
| Batch 27 | Catalase | PB-D | 10 | 2.5 | 0.167 | 0.667 | 1.333 | 3.667 | 72.89 ± 1.21 | 15.41 ± 0.22 |
| Batch 28 | Catalase | PB-D | 10 | 2.5 | 0.1 | 0.4 | 0.8 | 4.2 | 76.89 ± 1.18 | 16.12 ± 0.21 |

EXAMPLE 5

Drug Release from Pentablock Polymer Nanoparticles Dispersed in Pentablock Polymer Thermosensitive Gel In this example, 20% w/w of a thermosensitive gel comprising the pentablock polymer $PEG_{550}$-$PCL_{525}$-$PLA_{550}$-$PCL_{825}$-$PEG_{550}$ was solubilized in 10 mM PBS by keeping overnight at 4° C. Then 1 mg of IgG-Fab equivalent nanoparticles described in Example 3B were dispersed in 100 µL of 20% w/w thermosensitive polymer solution. The amount of nanoparticles required are calculated based on drug loading. Thus, the entire composition takes the form of an injectable formulation. Resulting suspension was incubated in 1.5 mL vial at 37° C. for 30 mM Once gel was solidified, 1 mL of PBS (pre-incubated at 37° C.) was slowly added. At predetermined time intervals, 0.2 mL of clear supernatant was collected and replaced with same volume of fresh PBS (pre-incubated at 37° C.). Release samples were analyzed by Micro BCA™ for total protein content. Micro BCA™ was performed according to supplier's instructions. In vitro release experiments were performed in triplicates and expressed as cumulative drug released (%) with time. The results are shown in FIG. 7.

PB-A, PB-C and PB-D were successfully employed for the preparation of IgG-Fab loaded NPs. As shown in Table 2, pentablock copolymers (PB-A, PB-C and PB-D) exhibited higher drug loading. These polymers (PB-A and PB-D) demonstrated very slow release rate (<2.5 µg/day) (FIG. 7). Therefore, these polymers are suitable for very potent drug or the conditions where lower rate of release is required for longer duration of time (about 8-10 months). However, these polymeric systems (PB-A or PB-D) are not useful where higher release rate with similar or higher drug loading is required. Therefore, there was a need to develop a formulation which can provide higher amount of release for at least 4 to 6 months.

Figure 7:
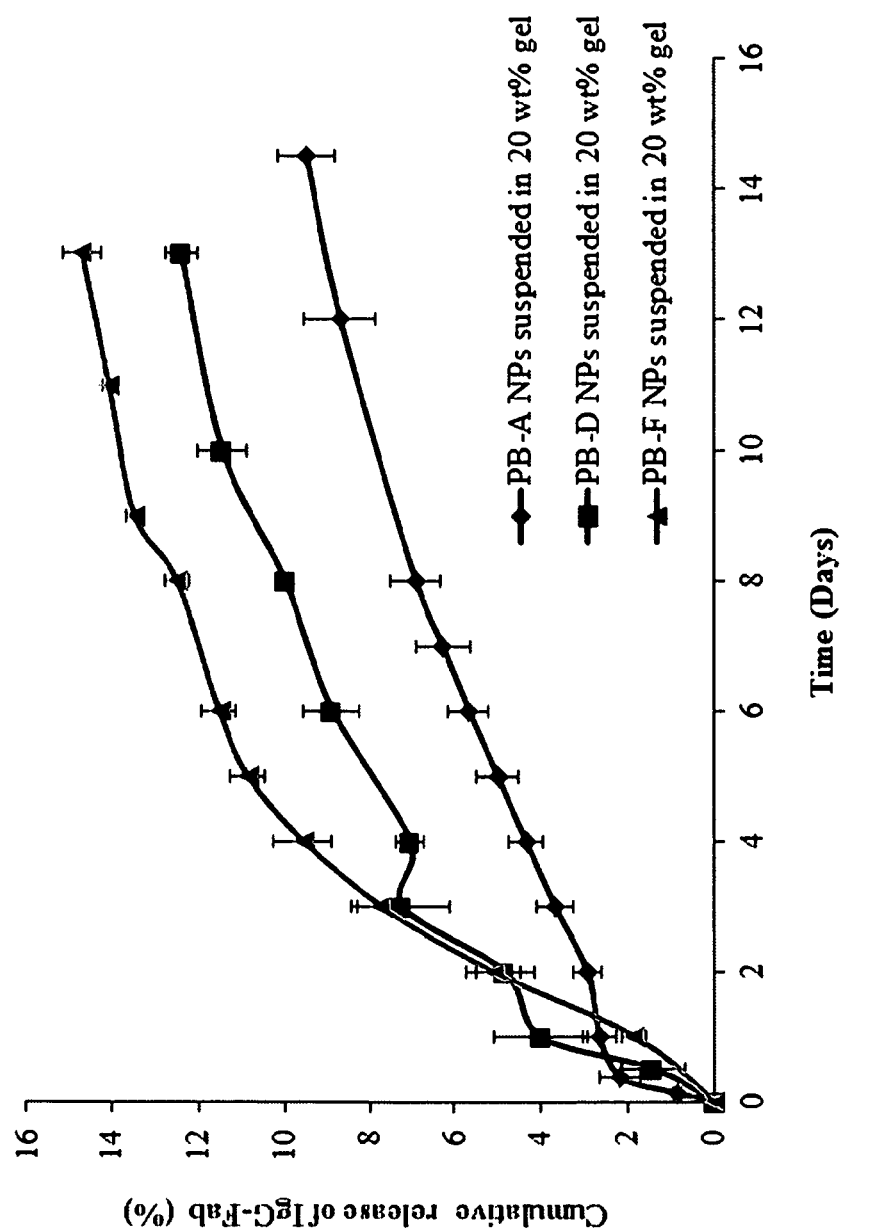
FIG. 7 shows the in vitro release of IgG-Fab from three different pentablock nanoparticles suspended in thermosensitive gel (20 wt %) (n=3) Pentablock Polymer A, $PGA_{3000}$-$PCL_{7000}$-$PEG_{2000}$-$PCL_{7000}$-$PGA_{3000}$ (Pentablock Polymer D), and Pentablock Polymer F.

As shown in FIG. 7, changing the sequence of blocks in pentablock copolymers (PCL-PLA-PEG-PLA-PCL, PB-F) resulted in high drug loading (~18.5%). Moreover, the PB-F nanoparticles suspended in thermosensitive gel (20 wt %) also offered significantly higher rate of release (>4.5 µg/day, FIG. 7) relative to PB-A or PB-D nanoparticles suspended in thermosensitive gel (20 wt %). With current rate of release, it is anticipated that PB-F nanoparticles will release IgG-Fab for about 4 to 6 months which will be ideal for many diseases conditions.

EXAMPLE 6

X-Ray Diffraction

Figure 6:
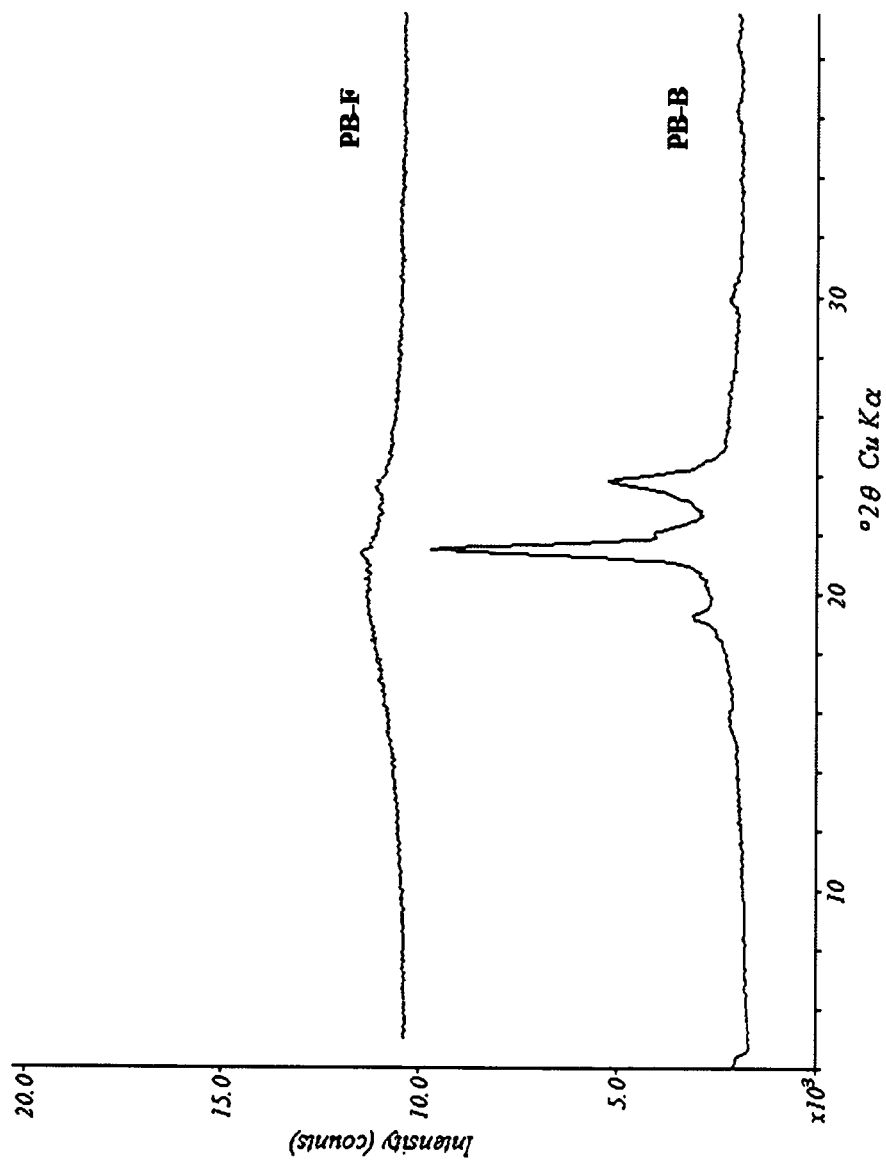
FIG. 6 shows the X-ray diffraction patterns of Pentablock Polymer B and Pentablock Polymer F

As shown above, synthesis of pentablock copolymers with modified sequence i.e., PCL-PLA-PEG-PLA-PCL, improves polymer degradation and subsequently rate of drug release. It is widely reported that rate of degradation for PLA is relatively faster than that of PCL. It was shown that the sequence of polymer blocks plays a critical role in determining the crystallinity of PB copolymers. As described in FIG. 6, conjugation of PLA at the terminal of PCL-PEG-PCL triblock copolymers exhibited peaks at 2θ=21.5° and 23.8° suggesting semi-crystalline polymer (PB-B). Interestingly, conjugation of PLA between the PCL and PEG blocks resulted in absence of any crystalline peaks indicating PB-F as an amorphous polymer. Previously published reports suggest that rate of polymer degradation is significantly influenced by crystallinity of polymer. Crystalline polymer degrades slowly relative to the amorphous polymer. Hence, this helps explain why faster degrading PB-F copolymer will provide relatively higher rate of drug release from PB-F nanoparticles compared to slowly degrading PB-A or PB-B copolymers based nanoparticles.

Results described in FIG. 7 demonstrate that release of IgG-Fab from PB-A nanoparticles suspended in thermosensitive gel is significantly lower relative to PB-F NPs suspended in thermosensitive gel. These might be attributed to amorphous nature of PB-F copolymer which may allow faster degradation of block copolymers resulting in higher rate of drug release. By changing the block sequences, rate of drug release and polymer degradation can be easily modulated, and adjusted according to desired target product profile (TPP).

From the foregoing it will be seen that this invention is one well adapted to attain all ends and objectives hereinabove set forth, together with the other advantages which are obvious and which are inherent to the invention. Since many possible embodiments may be made of the invention without departing from the scope thereof, it is to be understood that all matters herein set forth in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. A pentablock polymer according to the formula CBABC, comprising:
   polyethylene glycol (PEG);
   polyglycolic acid (PGA) or polylactic acid (PLA); and
   poly(ε-caprolactone) (PCL);
   wherein the pentablock polymer has a PCL-PLA-PEG-PLA-PCL configuration or PCL-PGA-PEG-PGA-PCL configuration.

2. The pentablock polymer according to claim 1, wherein the pentablock polymer has the PCL-PLA-PEG-PLA-PCL configuration and is defined according to:

$$PCL_C\text{-}PLA_B\text{-}PEG_A\text{-}PLA_B\text{-}PCL_C,$$

wherein PEG is polyethylene glycol;
wherein PLA is polylactic acid;
wherein PCL is poly(ε-caprolactone);
wherein A defines an average molecular weight of 200 to 20,000 Da;
wherein B defines an average molecular weight of 100 to 10,000 Da; and
wherein C defines an average molecular weight of 500 to 25,000 Da.

3. The pentablock polymer of claim 2 wherein the PEG is less than 30% by weight, the PLA is about 10 to 80% by weight, and the PCL is about 10 to 80% by weight.

4. The pentablock polymer according to claim 1, wherein the pentablock polymer has the PCL-PGA-PEG-PGA-PCL configuration and is defined according to:

$$PCL_F\text{-}PGA_E\text{-}PEG_D\text{-}PGA_E\text{-}PCL_F,$$

wherein PEG is polyethylene glycol;
wherein PGA is polyglycolic acid;

wherein PCL is poly(ε-caprolactone);
wherein D defines an average molecular weight of 200 to 20,000 Da;
wherein E defines an average molecular weight of 500 to 15,000 Da; and
wherein F defines an average molecular weight of 500 to 25,000 Da.

5. A nanoparticle comprising the pentablock polymer of claim 1.

6. The nanoparticle of claim 5 wherein the nanoparticle has a particle size of 300 to 700 nm.

7. A bioactive or diagnostic composition consisting essentially of the pentablock polymers claim 1 and an effective amount of a bioactive agent or diagnostic agent.

8. The bioactive or diagnostic composition of claim 7 wherein said bioactive agent or diagnostic agent comprises a protein or peptide.

9. The bioactive or diagnostic composition of claim 7 wherein said bioactive agent or diagnostic agent is 0.01 to 50 wt % of the composition.

10. A controlled release formulation comprising:
a plurality of nanoparticles, said nanoparticles comprising a drug or diagnostic agent encapsulated in a first pentablock polymer according to claim 1; and
a thermosensitive gel;
wherein said plurality of nanoparticles are dispersed in said thermosensitive gel.

11. The controlled release formulation of claim 10 wherein said thermosensitive gel comprises a second pentablock polymer.

12. The controlled release formulation of claim 11, wherein said second pentablock polymer is defined according to PEG-PCL-PLA-PCL-PEG, and wherein
the PLA has an average molecular weight of 100 to 5,000 Da;
the PCL has an average molecular weight of 100 to 1,000 Da; and
the PEG has an average molecular weight of 100 to 20,000 Da.

13. The controlled release formulation of claim 12, wherein for the second pentablock polymer, the PEG is about 10 to 50% by weight, the PCL is about 40 to 60% by weight, and the PLA is about 5 to 25% by weight.

14. The controlled release formulation of claim 10, wherein said drug or diagnostic agent comprises a protein or peptide.

15. The controlled release formulation of claim 10 wherein said nanoparticles consist essentially of the first pentablock polymer and said drug or diagnostic agent.

16. The controlled release formulation of claim 10 wherein said nanoparticles have a particle size of about 300 to 700 nm.

17. The controlled release formulation of claim 10 wherein said nanoparticles comprise said drug in an amount of about 0.01 to 50 wt %.

18. The controlled release formulation of claim 10 wherein said thermosensitive gel has a lower critical solution temperature below about 35° C.

19. A method for preparing bioactive or diagnostic agent loaded nanoparticles comprising the pentablock polymer of claim 1, wherein said method comprises:
emulsifying a $W_1$ solution in an organic solution O to form a $W_1/O$ primary emulsion, wherein said $W_1$ solution comprises a bioactive agent or diagnostic agent in an aqueous solution, and said organic solution O comprises an organic solvent and the pentablock polymer;
emulsifying said primary emulsion in an external water phase solution $W_2$ to obtain a $W_1/O/W_2$ double emulsion;
optionally diluting said $W_1/O/W_2$ double emulsion with an aqueous solution $W_3$ to form an optionally diluted $W_1/O/W_2$ double emulsion; and
removing said organic solvent to form said bioactive or diagnostic agent loaded nanoparticles from said optionally diluted $W_1/O/W_2$ double emulsion;
wherein said bioactive or diagnostic agent has a loading of about 10 to 25%.

20. The method of claim 19 wherein said method has an initial or nominal ratio of pentablock polymer to bioactive agent or diagnostic agent of about 10:1 to 2:1.

21. The method of claim 19, wherein said bioactive agent or diagnostic agent comprises IgG or IgG-Fab or an enzyme.

22. The method of claim 19 wherein said aqueous solution forming said $W_1$ solution is distilled deionized water, wherein said organic solution O comprises dichloromethane, wherein said external water phase solution $W_2$ comprises polyvinyl alcohol in distilled deionized water, and/or wherein said aqueous solution $W_3$ comprises polyvinyl alcohol in distilled deionized water.

23. The method of claim 19 wherein said isolating step comprises evaporating said organic phase in said optionally diluted emulsion.

24. The method of claim 19, wherein the nanoparticles have a particle size of about 300 to 700 nm.

25. The method of claim 19, wherein said bioactive or diagnostic agent loaded nanoparticles have a bioactive agent or diagnostic agent loading of about 10 to 25 wt %.

26. The method of claim 19, wherein said bioactive or diagnostic agent loaded nanoparticles have a bioactive agent or diagnostic agent entrapment efficiency of about 45 to 90%.

* * * * *